(12) United States Patent
Miller et al.

(10) Patent No.: US 10,888,683 B2
(45) Date of Patent: *Jan. 12, 2021

(54) RELATING TO BREATHING SYSTEMS

(71) Applicant: INTERSURGICAL AG, Vaduz (LI)

(72) Inventors: Andrew Miller, Bracknell (GB); Marc Berrow Gibbons, Wokingham (GB)

(73) Assignee: INTERSURGICAL AG, Vaduz (LI)

( * ) Notice: Subject to any disclaimer, the term of this patent is extended or adjusted under 35 U.S.C. 154(b) by 230 days.

This patent is subject to a terminal disclaimer.

(21) Appl. No.: 16/014,810

(22) Filed: Jun. 21, 2018

(65) Prior Publication Data
US 2018/0296789 A1  Oct. 18, 2018

Related U.S. Application Data

(63) Continuation of application No. 13/991,265, filed as application No. PCT/GB2011/052124 on Nov. 1, 2011, now Pat. No. 10,029,059.

(30) Foreign Application Priority Data

Dec. 3, 2010 (GB) .................................. 1020496.4

(51) Int. Cl.
*A61M 16/10* (2006.01)
*A61M 16/08* (2006.01)
(Continued)

(52) U.S. Cl.
CPC .... *A61M 16/1045* (2013.01); *A61M 16/0057* (2013.01); *A61M 16/0415* (2014.02);
(Continued)

(58) Field of Classification Search
CPC .. A61M 16/0057; A61M 16/01; A61M 16/08; A61M 16/0808; A61M 16/0883;
(Continued)

(56) References Cited

U.S. PATENT DOCUMENTS 2,381,006 A  8/1945  Scott, Jr.
4,417,574 A  11/1983  Talonn et al.
(Continued)

FOREIGN PATENT DOCUMENTS

CN  1958087 A  5/2007
DE  102005062185 B3  7/2007
(Continued)

OTHER PUBLICATIONS

Search Report for GB1118856.2 dated Feb. 3, 2012.
(Continued)

*Primary Examiner* — Joseph D. Boecker
(74) *Attorney, Agent, or Firm* — Troutman Pepper Hamilton Sanders LLP (Rochester)

(57) ABSTRACT

Apparatus (10,226,326) for condensing water from respiratory gases, comprising a heat exchange component (20,234,334) having an inlet (22,228,328), an outlet (24,228,230) and a condensation chamber, the inlet and outlet (22,24,228,230,328,330) being connectable to a breathing system, such that respiratory gases are conveyed through the condensation chamber, in use, and a base unit (30,232,332) adapted to aid removal of heat from the walls of the heat exchange component (20,234,334), wherein the heat exchange component (20,234,334) is releasably engageable with the base unit (30,232,332), such that the heat exchange component (20,234,334) is replaceable.

16 Claims, 14 Drawing Sheets

(51) Int. Cl.
*A61M 16/00* (2006.01)
*A61M 16/20* (2006.01)
*A61M 16/04* (2006.01)

(52) U.S. Cl.
CPC ........ *A61M 16/0808* (2013.01); *A61M 16/20* (2013.01); *A61M 2205/3673* (2013.01)

(58) Field of Classification Search
CPC .......... A61M 16/0891; A61M 16/1045; A61M 16/1075; A61M 2205/12; A61M 2205/121; A61M 2205/123; A61M 2205/128; A61M 2205/3673
See application file for complete search history.

(56) References Cited

U.S. PATENT DOCUMENTS

| | | | |
|---|---|---|---|
| 4,430,994 A * | 2/1984 | Clawson | A61M 16/16 128/203.27 |
| 4,506,510 A * | 3/1985 | Tircot | B01D 5/0042 62/3.4 |
| 4,951,659 A * | 8/1990 | Weiler | A61M 15/00 128/200.18 |
| 5,101,821 A | 4/1992 | Carie, Jr. | |
| 5,327,743 A | 7/1994 | Coltrin | |
| 5,398,677 A | 3/1995 | Smith | |
| 5,722,393 A | 3/1998 | Bartel et al. | |
| 6,523,538 B1 | 2/2003 | Wikefeldt | |
| 6,810,948 B2 * | 11/2004 | Peterson | F28D 7/06 165/111 |
| 7,128,135 B2 | 10/2006 | Mok et al. | |
| 7,591,267 B2 | 9/2009 | Mashak et al. | |
| 7,798,204 B2 | 9/2010 | Schoell | |
| 8,439,036 B2 | 5/2013 | Winter et al. | |
| 8,439,037 B2 | 5/2013 | Winter et al. | |
| 8,469,030 B2 | 6/2013 | Rossi et al. | |
| 8,469,031 B2 | 6/2013 | Winter et al. | |
| 9,205,221 B2 | 12/2015 | Winter et al. | |
| 9,669,181 B2 | 6/2017 | Miller | |
| 10,029,059 B2 * | 7/2018 | Miller | A61M 16/1045 |
| 2007/0051367 A1 | 3/2007 | Mashak et al. | |
| 2007/0157929 A1 | 7/2007 | Radomski et al. | |
| 2008/0009761 A1* | 1/2008 | Acker | A61B 5/411 600/532 |
| 2008/0105404 A1 | 5/2008 | Luo | |
| 2008/0174964 A1 | 7/2008 | Zhou et al. | |
| 2008/0236577 A1 | 10/2008 | Power et al. | |
| 2009/0038615 A1 | 2/2009 | Bradley | |
| 2010/0012127 A1 | 1/2010 | Roth et al. | |
| 2010/0294279 A1 | 11/2010 | Ionascu et al. | |
| 2011/0126832 A1 | 6/2011 | Winter et al. | |
| 2011/0126835 A1 | 6/2011 | Winter et al. | |
| 2011/0277541 A1 | 11/2011 | Kadle et al. | |
| 2014/0276176 A1 | 9/2014 | Winter | |
| 2016/0058969 A1 | 3/2016 | Winter et al. | |

FOREIGN PATENT DOCUMENTS

| | | |
|---|---|---|
| EP | 2335760 A1 | 6/2011 |
| JP | 01-501521 A | 6/1989 |
| JP | 2002-349273 | 4/2002 |
| JP | 2006-214696 A | 8/2006 |
| JP | 2006-325751 A | 12/2006 |
| JP | 2010-46107 A | 3/2010 |
| JP | 2010-506683 A | 3/2010 |
| WO | 91/14476 A1 | 10/1991 |
| WO | 2001/049351 A2 | 7/2001 |
| WO | 2007096649 A1 | 8/2007 |
| WO | 2011058371 A1 | 5/2011 |

OTHER PUBLICATIONS

PCT International Search Report for PCT/GB2011/052124, dated Feb. 2, 2012.

Notice of Allowance for U.S. Appl. No. 14/355,514, dated Feb. 14, 2017.

* cited by examiner

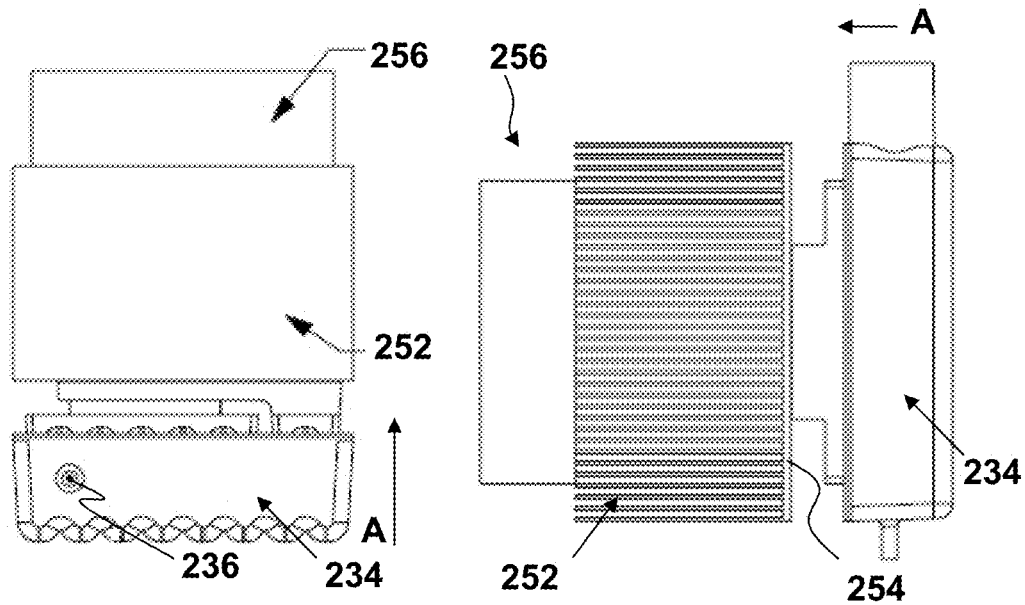
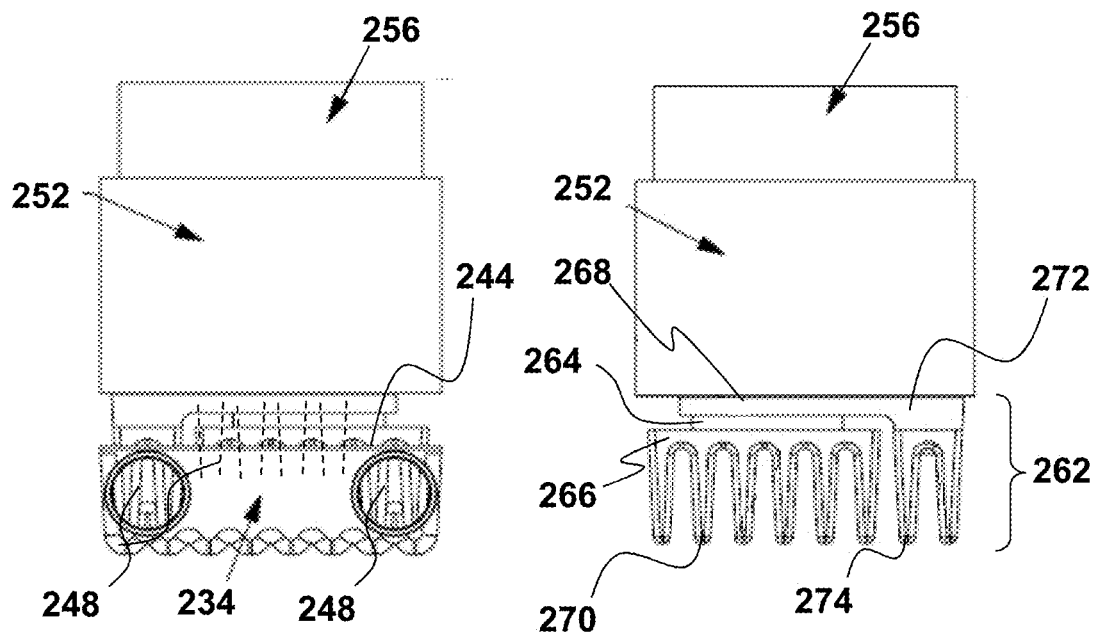
Figure 17
Figure 18
Figure 19
Figure 20

RELATING TO BREATHING SYSTEMS

This application is a continuation of U.S. patent application Ser. No. 13/991,265, which is a national stage application under 35 U.S.C. § 371 from PCT Application No. PCT/GB2011/052124, filed Nov. 1, 2011, which claims the priority benefit of Great Britain Application No. 1020496.4, filed Dec. 3, 2010, which are hereby incorporated by reference in their entirety.

This invention relates to breathing systems, and in particular to the management of water vapour and water condensate in breathing systems.

In a healthy person, the function of breathing is entirely spontaneous. The brain senses a build-up of carbon dioxide in the blood and immediately calls for more oxygen. This oxygen is taken into the body by spontaneous inspiration and carbon dioxide is removed in the passive exhalation phase of respiration. A healthy person generates a certain amount of humidity, which is used in the lung to stop the build-up of secretions.

The ability to breathe spontaneously may be lost for a number of reasons. Examples are as a result of surgical procedures (post-operatively), as a result of certain muscular disorders affecting the lung, or as a result of sedation by a clinician. Patients thus affected must be ventilated by mechanical means in order to achieve oxygenation and carbon dioxide removal.

When a patient is mechanically ventilated, it is essential that the humidity of the air is maintained at a sufficiently high level, since a lung with impaired function will be more susceptible to secretions. This is conventionally achieved using a heat-moisture exchanger (HME) or a heated water bath humidifier. An HME retains the moisture in an exhaled breath and this moisture is sent back to the lung with the next inspiratory phase. In a water bath system, the inspiratory gas is passed through a heated water chamber and picks up humidity prior to entering the lung.

As humid respiratory gases travel through a breathing system, either in the inspiratory limb or the expiratory limb of a breathing circuit, a certain amount of water vapour will cool and start to condense, forming water droplets, which will start to build up, causing so-called "rain-out".

It is important to remove water condensate from the breathing system, so that it does not occlude the respiratory air flow or drain back into the patient's lungs thereby putting the patient at risk of drowning, or does not drain into the ventilator/anaesthetic equipment thus causing damage. If it is allowed to accumulate for a protracted period then due to its non-compressible nature the water will effectively block the breathing system.

The conventional arrangement for managing moisture in such a system is by the use of a device called a water trap. Such a device is generally located at the mid-point of the breathing system and positioned at the lowest point so that liquid will drain into it. Periodically, the accumulated condensate is emptied and the water trap replaced. However, this arrangement is not entirely satisfactory because water condensate still forms within the breathing system, and this water condensate may interfere with the operation of valves, sensors or ventilation machinery of the system. In particular, in conventional arrangements, it is common for water condensate to accumulate at the ventilator exhalation valve, for example. This can cause problems with flow measurement, resistance to flow, false triggering of alarms, and indeed occlusion of tubes.

It is also known to attempt to dehumidify the respiratory gases within a breathing circuit, for example before the respiratory gases are delivered back to the ventilator. One such arrangement is an exhalation breathing tube with an enclosing wall that allows the passage of water vapour therethrough, but prevents the passage of respiratory gases. However, these exhalation breathing tubes are expensive to manufacture, and typically only remove a portion of the water vapour content from the respiratory gases. In addition, use of these exhalation breathing tubes results in water vapour that has been exhaled from a patient entering ambient air, which is then inhaled by clinicians.

There has now been devised apparatus which overcomes or substantially mitigates the above-mentioned and/or other disadvantages associated with the prior art.

According to a first aspect of the invention, there is provided apparatus for condensing water from respiratory gases, comprising a heat exchange component having an inlet, an outlet and a condensation chamber, the inlet and outlet being connectable to a breathing system, such that respiratory gases are conveyed through the condensation chamber, in use, and a base unit adapted to aid removal of heat from the walls of the heat exchange component, wherein the heat exchange component is releasably engageable with the base unit, such that the heat exchange component is replaceable.

According to a further aspect of the invention, there is provided a heat exchange component for condensing water from respiratory gases having an inlet, an outlet and a condensation chamber, the inlet and outlet being connectable to a breathing system, such that respiratory gases are conveyed through the condensation chamber, in use, wherein the heat exchange component is releasably engageable with a base unit adapted to aid removal of heat from the walls of the heat exchange component.

According to a further aspect of the invention, there is provided a base unit for use with a heat exchange component for condensing water from respiratory gases, the base unit being adapted to releasably engage the heat exchange component, and the base unit being adapted to aid removal of heat from the walls of the heat exchange component.

The apparatus according to the present invention is advantageous principally because the apparatus condenses water from respiratory gases within a heat exchange component, which enables the water to be removed from the breathing system. The present invention therefore reduces the risk that water condensate will form in the breathing system that will interfere with the operation of valves, sensors or ventilation machinery of the system.

Furthermore, the respiratory gases are conveyed through a heat exchange component that is releasably engageable with the base unit, such that the heat exchange component is replaceable. This enables the base unit to be arranged not to come into contact with the respiratory gases or water condensate, and hence enables the base unit to be a reusable component, with the heat exchange component being a disposable component. This is advantageous as it means the apparatus can be used safely and cost effectively with multiple patients by replacing the heat exchange component between patients. In addition, the present invention is less expensive than arrangements in which the entire apparatus is disposable.

Indeed, where the apparatus and/or base unit include means for actively cooling the respiratory gases conveyed through the condensation chamber, in use, for example by transferring heat from the walls of the heat exchange component, the present invention provides particular cost benefits. In particular, the heat transfer device, eg a Peltier device, is preferably provided in the base unit of the present invention, and hence may be reused. Furthermore, the heat exchange component of the present invention is preferably of simple construction, eg formed from two moulded parts, and hence inexpensive to manufacture.

The apparatus according to the invention is adapted to condense water from respiratory gases. Most preferably, the apparatus includes an arrangement for removing the water condensate from the breathing system. The apparatus is preferably therefore suitable for removing water condensate from a breathing system, and preferably includes an arrangement for collecting the water condensate for removal.

The heat exchange component includes a condensation chamber, through which respiratory gases are conveyed, in use. The condensation chamber is preferably adapted to promote heat transfer from the respiratory gases, to the walls of the condensation chamber, such that water is condensed from the respiratory gases, within the condensation chamber, in use. In particular, the condensation chamber preferably has an increased interior surface area relative to a single flow passageway having a generally circular cross-section. In presently preferred embodiments, the condensation chamber has a major wall that is substantially corrugated in form.

The condensation chamber may have a plurality of flow passageways, which are each adapted to convey respiratory gases, in use. The cross-sectional shape of the condensation chamber, or each flow passageway of the condensation chamber, may be adapted to provide an increased interior surface area relative to that provided by a circular cross-section. In some embodiments, the condensation chamber comprises a plurality of flow passageways, which each have an elongated, internal cross-sectional shape. For example, the ratio of the internal width of the flow passage to the internal depth of the flow passage may be at least 1:2, at least 1:3, at least 1:7, or about 1:10 or more.

The base unit is adapted to aid removal of heat from the walls of the heat exchange component. The base unit is preferably arranged to reduce the temperature of the respiratory gas flow downstream of the inlet. The base unit is preferably adapted to cool the respiratory gases within the condensation chamber. This may be achieved in a variety of ways. In particular, the base unit may include a cooler arranged to cool the respiratory gases actively. The cooler may be connectable to a power supply, and may provide transfer of heat away from the condensation chamber, for example to another part of the apparatus and/or the surroundings, eg via a heat sink. The base unit may include a surface of reduced temperature, relative to ambient temperature. This surface of reduced temperature may be adapted to reduce the temperature of the air surrounding the heat exchange component, or may be adapted to contact exterior surface(s) of the heat exchange component.

The base unit may comprise a heat exchange medium arranged to transfer heat energy away from the condensation chamber. The base unit may comprise a thermoelectric member for cooling the respiratory gases within the condensation chamber. The thermoelectric member may be arranged to provide thermal communication away from the condensation chamber, for example to another part of the apparatus and/or the surroundings, eg via a heat sink. The thermoelectric member may be connectable to a power source such that it is arranged to drive heat transfer away from the condensation chamber.

The thermoelectric member may comprise a Peltier device.

In presently preferred embodiments, the base unit comprises a heat exchange medium, eg a thermoelectric member, having a cold side and a hot side, the cold side being arranged for thermal contact with the condensation chamber of the heat exchange component adapted to aid removal of heat from the walls of first portion. As discussed in more detail below, the base unit may also be arranged such that the hot side is in thermal contact with a heater chamber of the heat exchange component, downstream of the first portion, in order to heat the respiratory gases prior to those gases exiting the heat exchange component.

Alternatively, or in addition, the apparatus may be adapted to promote transfer of heat from the respiratory gases to the surroundings, ie to provide passive cooling, for example by providing a condensation chamber with an exterior of increased surface area, for a given volume, relative to a single flow passageway of substantially circular cross-section. The base unit may be adapted to generate an air flow across external surface(s) of the heat exchange component. This air flow may increase the rate of conduction of heat away from the external surface(s) of the heat exchange component by causing air to which heat from the those surfaces has been conducted, and hence air that is at a raised temperature relative to ambient air, to be continuously replaced with air at a lower temperature. The air flow generated by the base unit may be ambient air, or may be at a reduced temperature relative to ambient air.

The flow of air, eg ambient air, across external surface(s) of the heat exchange component may be generated by an electric fan, which may be housed within the base unit. The fan may be adapted to generate a flow of air that flows over external surface(s) of the heat exchange component, and is then dissipated into the surroundings. The air flow generated by the base unit may be blown across external surface(s) of the heat exchange component, or may alternatively be drawn across external surface(s) of the heat exchange component, by the base unit, eg by the electric fan. Once the air flow has traveled across external surface(s) of the heat exchange component, the air flow may be directed away from the user, in use. In one embodiment, the base unit is adapted to draw a flow of air across external surface(s) of the heat exchange component, which is located at the front of the apparatus relative to the user, eg relative to the clinician, and the base unit is adapted to dissipate this air flow into the surroundings at the rear of the base unit.

The condensation chamber may also be adapted to promote heat transfer from the walls of heat condensation chamber, to ambient air, in use. In particular, the condensation chamber may adapted for effective cooperation with the base unit. For example, it is generally preferred that the condensation chamber has an increased exterior surface area relative to a single flow passageway having a generally circular cross-section. In presently preferred embodiments, the condensation chamber has a major wall that is substantially corrugated in form.

The condensation chamber may comprise a plurality of flow passageways, which are each adapted to convey respiratory gases, in use. The cross-sectional shape of the condensation chamber, or each flow passageway of the condensation chamber, may be adapted to provide an increased exterior surface area relative to that provided by a circular cross-section. In some embodiments, the condensation chamber comprises a plurality of flow passageways, which each have an elongated, exterior cross-sectional shape. For example, the ratio of the exterior width of the flow passage to the exterior depth of the flow passage may be at least 1:2, at least 1:3, at least 1:7, or about 1:10 or more.

Where the base unit is adapted to generate a flow of air across external surface(s) of the heat exchange component, as described above, the condensation chamber may have an increased exterior surface area that is exposed to that air flow, relative to a single flow passageway having a generally circular cross-section. Hence, in addition to having an arrangement as described above to provide an increased exterior surface area, the condensation chamber may be arranged relative to the base unit to expose at least 50%, at least 60%, or at least 80% of its total exterior surface area to the air flow generated by the base unit. In this embodiment, the condensation chamber may be arranged relative to the base unit with the major exterior surfaces of its flow passageway(s) substantially aligned with the air flow generated by the base unit. The condensation chamber may comprises a plurality of flow passageways, which are separated from one another to define one or more exterior passageways through the heat exchange component. The condensation chamber may be arranged relative to the base unit such that the air flow from the base unit is conveyed through the one or more exterior passageways. The one or more exterior passageways may be substantially aligned with the direction of flow of air from the base unit.

Where the base unit is adapted to generate a flow of air across external surface(s) of the heat exchange component, the condensation chamber may comprise a plurality of flow passageways, each generally planar in form, which are aligned adjacent and parallel to each other, and which are separated from one another to define exterior flow passages therebetween. When engaged with the base unit, each exterior passageway may be substantially aligned with the direction of flow of air from the base unit.

The inlet and outlet of the heat exchange component preferably each have the form of a conventional tubular connector for connection to other components of breathing systems. In addition, however, the inlet and/or outlet may include an arrangement for deflecting incoming and/or outgoing respiratory gases transversely relative to the central axis of the port(s). This arrangement may comprise a baffle, which may be arranged adjacent to the exit of the port, and may be aligned with the port, such that air is deflected around the baffle, in use.

The arrangement for collecting the water condensate for removal is preferably separate from the breathing system, such that water condensing within the heat exchange component does not re-enter the breathing system. Hence, the heat exchange component preferably has the inlet and the outlet formed in an upper portion of the component, for example at the upper end, in order to prevent the flow of water condensate into the connected breathing system.

The heat exchange component may itself be adapted to collect water condensate for removal, for example by incorporating the inlet and outlet into a valve arrangement that enables disconnection of the heat exchange component from the breathing system, without enabling escape of respiratory gases. In presently preferred embodiments, however, the heat exchange component is preferably adapted for connection to a separate arrangement for collecting the water condensate for removal.

The heat exchange component preferably includes a water condensate outlet port, which is adapted to enable the removal of water condensate from the heat exchange component, and most preferably from the breathing system. The water condensate outlet port preferably allows the flow of water condensate out of the heat exchange component, without allowing the flow of respiratory gases through the port. Most preferably, the water condensate outlet port includes a float valve, which allows the flow of water condensate out of the heat exchange component when the level of water condensate within the heat exchange component is at or above a threshold level.

The heat exchange component is connectable to a breathing system, such that respiratory gases are conveyed through the condensation chamber, in use. Hence, according to a further aspect of the invention, there is provided a breathing system comprising apparatus as described above.

The breathing system is preferably a breathing circuit, which will typically include at least a ventilator or an anesthesia machine, and an inspiratory limb. However, the present invention is particularly advantageous for removing water from exhaled gases, and hence the breathing circuit preferably also includes an expiratory limb, and the apparatus according to the invention is preferably connected within the breathing circuit, such that it forms part of that limb. In particular, the expiratory limb preferably comprises at least two breathing tubes, with the heat exchange component connected between those breathing tubes, preferably at the lowest point of the expiratory limb.

The apparatus according to the invention may also include a device for heating the respiratory gases in the expiratory limb, which is disposed between the heat exchange component and the ventilator or anesthesia machine. This device is preferably adapted to maintain the respiratory gases above their dew point, thereby enabling further condensation to be reduced or prevented. Alternatively, or in addition, the apparatus may be adapted to heat the respiratory gases to a temperature above their dew point before the gases exit the heat exchange component. This arrangement reduces the likelihood that any remaining vapour within the respiratory gases will condense out of the gas flow within another portion of the breathing system.

The heat exchange component is preferably a disposable component, which is preferably formed of plastics material. The heat exchange component preferably forms a closed system, relative to the base unit, such that there is no contact between the base unit, or any air flow generated by the base unit, and the respiratory gases of the breathing system.

The heat exchange component and the base unit preferably include formations that cooperate to mount the heat exchange component relative to the base unit. In particular, the heat exchange component may be slidably engaged with the base unit, which may be achieved by means of cooperating rails and grooves. In presently preferred embodiments, the heat exchange component is engageable with the base unit from above. In this arrangement, the heat exchange component is retained by the action of gravity. However, a fastening arrangement may be provided.

In presently preferred embodiments, the base unit includes a recess, such that the heat exchange component is mounted within the recess of the base unit. In any event, at least one major surface of the heat exchange component is preferably exposed to the surroundings.

Where the base unit includes a heat exchange medium for transferring heat away from the heat exchange component, eg the condensation chamber, and/or transferring heat to the heat exchange component, eg the heater chamber, the base unit preferably includes one or more heat conductors for engaging the exterior surface of the heat exchange component. In presently preferred embodiments, the one or more heat conductors take the form of projections or recesses for engaging corresponding, eg mating, projections or recesses of the heat exchange component.

The base unit is preferably a re-usable component, and will typically include a connection to a power supply.

As described above, the heat exchange component preferably includes a water condensate outlet port, which is adapted to enable the removal of water condensate from the heat exchange component, and most preferably from the breathing system. The apparatus according to the invention preferably includes an arrangement for collecting the water condensate for removal, which is engageable with the water condensate outlet port of the heat exchange component. In particular, the apparatus according to the invention preferably includes a sump component that is removably connected to the water condensate outlet port of the heat exchange component, where the sump component may have the form of a bag, a vessel, or any other type of suitable container. Most preferably, the interior of the sump component is expandable, such that the interior may be substantially evacuated prior to use.

The sump component may be connected directly to the water condensate outlet port, or may be connected via tubing for transporting the water condensate. The apparatus preferably also includes an arrangement for closing the water condensate outlet port when the sump component is removed for emptying or disposal. This closure arrangement may take the form of a valve in the water condensate outlet port. In a preferred embodiment, the valve includes one or more duckbill valves, which are maintained in an open configuration by the presence of the sump component in connection with the heat exchange component, and which revert to a closed configuration when the sump component is disconnected from the heat exchange component. For example, the sump component may be adapted to cause the movement of resiliently movable, outwardly extending arms of the valve on connection of the sump component to the heat exchange component. In a particularly preferred embodiment, the valve includes two duckbill valves, which are coupled by a connection member, such that connection of the sump component to the heat exchange component causes both duckbill valves to open As described above, the apparatus may be adapted to heat the respiratory gases to a temperature above their dew point before the gases exit the heat exchange component. This arrangement reduces the likelihood that any remaining vapour within the respiratory gases will condense out of the gas flow within another portion of the breathing system.

In this embodiment, the heat exchange component may comprise a condensation chamber and a heater chamber, the condensation and heater chambers being arranged in flow series.

According to a further aspect of the invention, there is provided a base unit for use with a replaceable heat exchange component for condensing water from respiratory gases, the base unit being adapted to releasably engage the heat exchange component, and the base unit comprising a heat exchange device having a cold side and a hot side, the cold side being arranged for thermal contact with a first portion of the heat exchange component and the hot side being arranged for thermal contact with a second portion of the heat exchange component.

According to a further aspect of the invention, there is provided a heat exchange component for condensing water from respiratory gases, the component having a condensation chamber portion having an inlet and a heater chamber portion having an outlet, the inlet and outlet being connectable to a breathing system, wherein the condensation chamber portion and the heater chamber portion are in fluid communication such that respiratory gases are conveyed from the inlet through condensation and heater chamber portions in use prior to passing through the outlet, wherein the heat exchange component is releasably engageable with a base unit adapted to aid removal of heat from the condensation chamber and/or aid provision of heat energy to the heater chamber portion.

The apparatus may therefore comprise a condenser including the condensation chamber and a heater including the heater chamber, the heater being downstream of the condenser for increasing the temperature of the respiratory gas flow prior to the outlet.

The heater may be adapted so as to raise the temperature of the respiratory gas flow to a temperature greater than its dew point prior to passing through the outlet. The heater may be adapted to heat the respiratory gases passively, but the heater is preferably adapted to heat the respiratory gases actively. The heater may be adapted to generate heat, which is transferred to the respiratory gas flow. The heater may produce a substantially constant amount of heat, such that there is no control of the heater, eg the heater is provided with a constant power supply. Alternatively, the apparatus may include a controller for the heater, for example to provide the respiratory gas flow with a predetermined temperature, or range of temperatures, at the outlet. This controller may control the power supplied to the heater, and may utilise one or more sensors for enabling feedback control.

The condenser may be arranged to reduce the temperature of the respiratory gas flow downstream of the inlet, and upstream of the heater. The condenser may be adapted to cool the respiratory gases within the condensation chamber. The condenser may be adapted to promote transfer of heat from the respiratory gases to the surroundings, ie to provide passive cooling, for example by providing a condensation chamber with an exterior of increased surface area, for a given volume, relative to a single flow passageway of substantially circular cross-section. Alternatively, or in addition, the condenser may include a cooler arranged to cool the respiratory gases actively. The cooler may be connectable to a power supply, and may provide transfer of heat from the condenser to the heater and/or a heat sink.

The temperature of the gas passing through the outlet may be greater than the temperature of the gas in the condenser. The condenser may be arranged to reduce the temperature of the respiratory gas flow to a temperature less than or equal to its dew point, and the heater may be adapted so as to raise the temperature of the respiratory gas flow to a temperature greater than its dew point.

The condensation chamber and the heater chamber may comprise different regions of a common chamber or enclosure. The heat exchange component may form a common housing for the condensation chamber and the heater chamber. The condensation chamber and the heater chamber may comprise a plurality of heat conducting walls.

The base unit may comprise a heat exchange medium arranged to transfer heat energy from the condenser to the heater. The heater and condenser may share a common heat exchange medium. Such an arrangement is advantageous in that the energy consumed by the apparatus in use is reduced by re-heating the gas flow using the heat energy removed from the flow by the condenser.

The base unit may comprise a thermoelectric member. The thermoelectric member may be arranged to provide thermal communication between the condenser and heater. The thermoelectric member may be connectable to a power source such that it is arranged to drive heat transfer from the condenser to the heater. The condenser may comprise a cold side of the thermoelectric member and the heater may comprise a hot side of the thermoelectric member.

The thermoelectric member may comprise a Peltier device.

Either of the condensation and heater chambers may comprise heat exchange members arranged to protrude into the path of the flow through the apparatus. The heat exchange members may comprise one or more upstanding walls arranged to define one or more flow passages through the condensation chamber and/or the heater chamber. The upstanding walls may take the form of baffles which may be arranged so as to define a tortuous flow path through the condensation chamber and/or the heater chamber. In one embodiment, the first and second portions are defined by a chamber with at least one wall being formed with inwardly projecting members, for example at least one wall may include corrugated portions.

One of the condensation chamber and the heater chamber may have a volume which is larger than that of other. A length, width or depth dimension of one of the chambers may be greater than that of the other chamber. Accordingly the time taken for the flow to pass through one of the chambers may be greater than the time taken for the flow to pass through the other chamber. One of the chambers may have a heat exchange surface area exposed to the flow there-through which is greater than the heat exchange surface area of the other chamber. Alternatively, the volume, dimensions and/or flow period may be equal for the chambers.

Even where the base unit comprises a heat exchange medium or thermoelectric member for transferring heat from the condenser to the heater, the apparatus may produce excess heat. The apparatus may include a heat sink for removing excess heat from the apparatus. The heat sink may be external of any condenser and/or heater chamber of the apparatus, and is preferably formed on the base unit. The heat sink may comprise a plurality of heat exchange elements, which may be exposed to ambient air. The heat sink may comprise a fan arranged to create a flow of ambient air over the heat exchange elements. The heat sink may be arranged to dissipate heat energy from the system to ambient air.

Any of the preferable features described above in relation to any one aspect of the invention may be applied to any further aspect of the invention wherever practicable.

Preferred embodiments of the invention will now be described in greater detail, by way of illustration only, with reference to the accompanying drawings, in which;

FIG. 17 is an underside view of the second embodiment;

FIG. 18 is a side view of the second embodiment;

FIG. 19 is a plan view of the second embodiment;

FIG. 20 is an underside view of the second embodiment with the cartridge removed;

FIGS. 1 to 4 each show a first embodiment of apparatus according to the invention, which is generally designated 10. The apparatus 10 comprises a radiator component 20 and a fan unit 30. The radiator component 20 is a replaceable and disposable component, which is adapted to form part of an exhalation limb of a respiratory circuit, as described in more detail below. The fan unit 30, however, is a reusable electrical component, with which the radiator component 20 is releasably engaged, in use.

Figure 1:
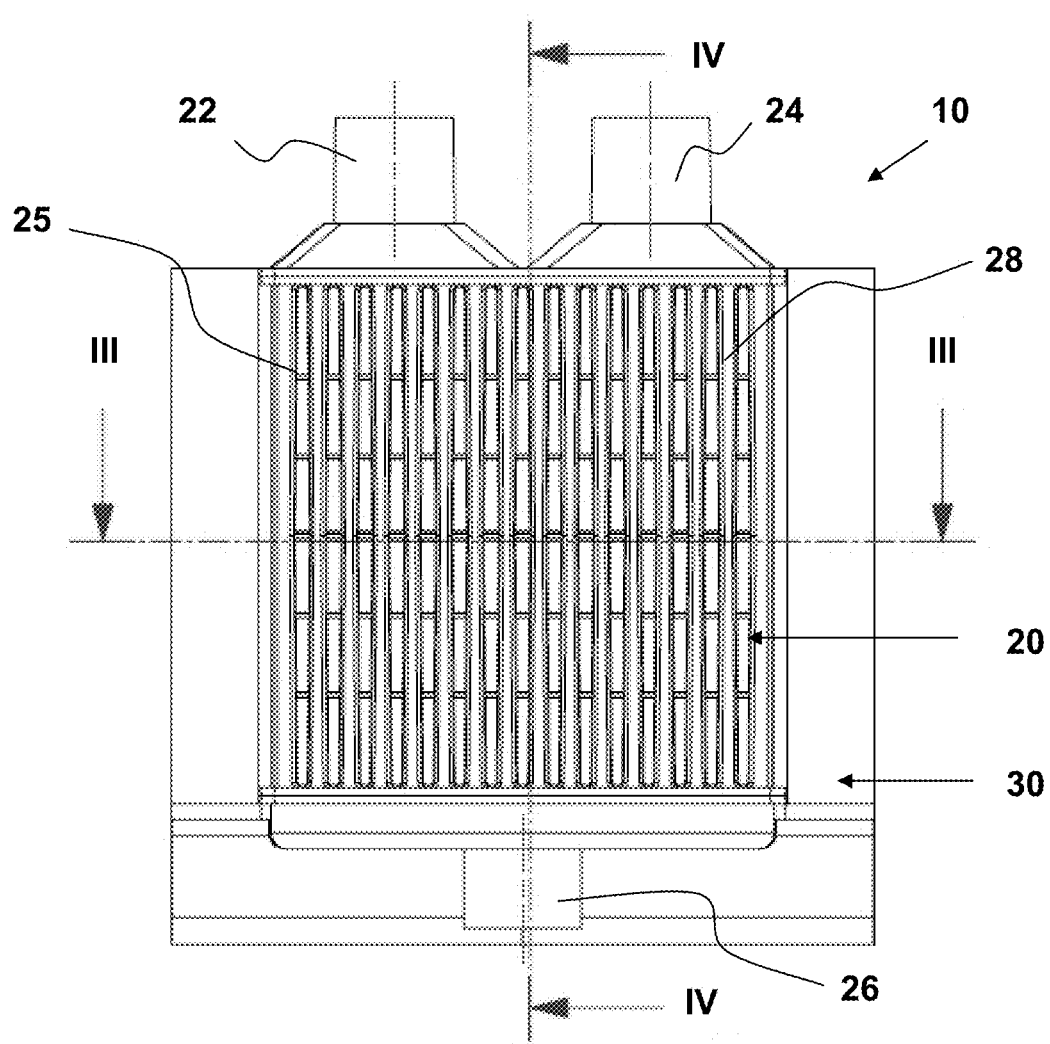
FIG. 1 is a front view of a first embodiment of apparatus according to the invention.
Figure 2:
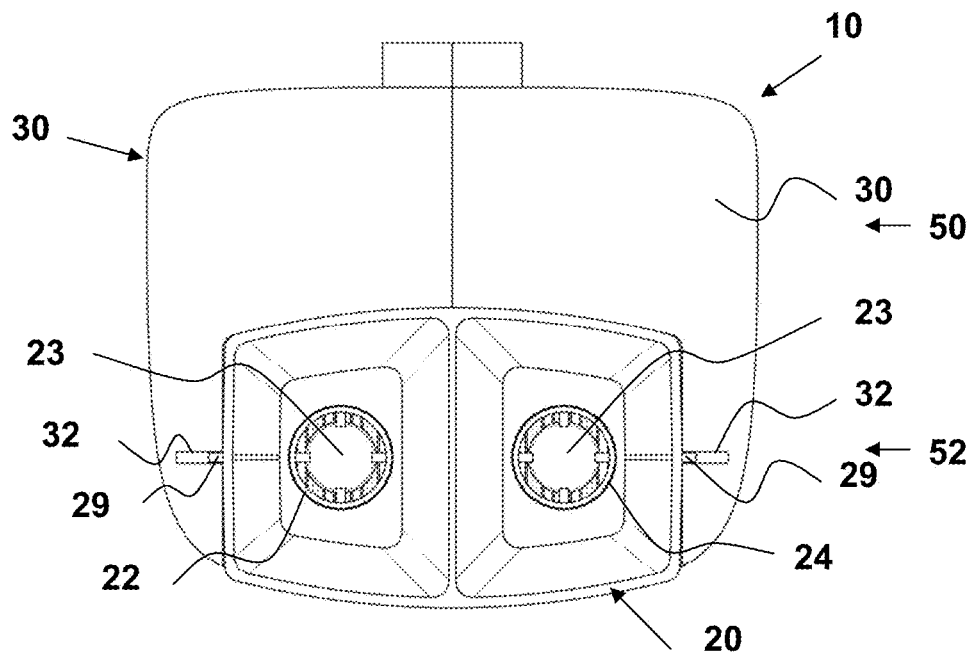
FIG. 2 is a plan view of the apparatus of FIG. 1.
Figure 9:
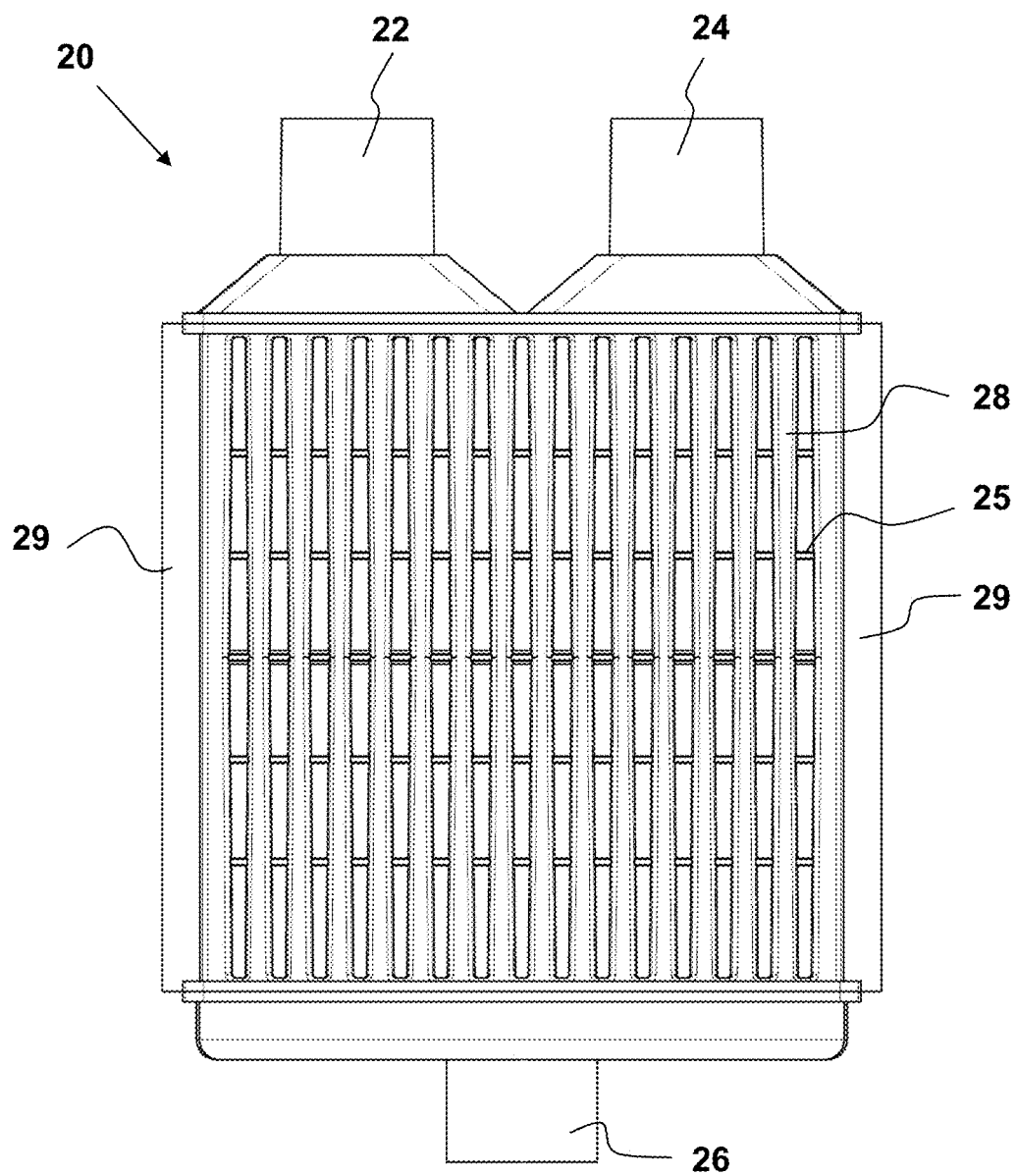
FIG. 9 is a front view of the radiator component, which forms part of the apparatus according to the invention.
Figure 10:
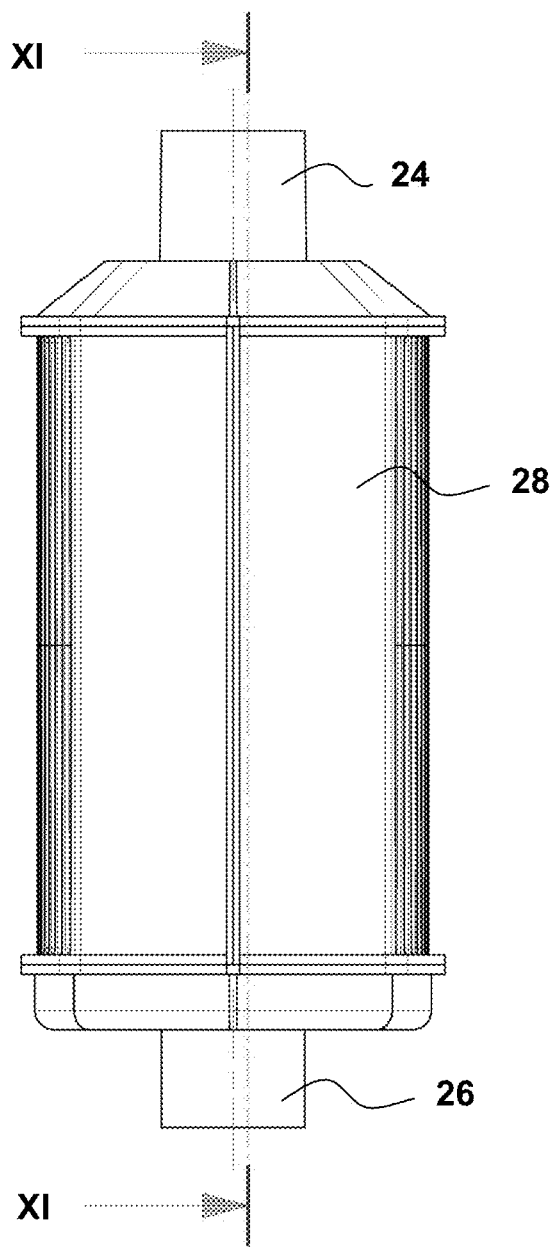
FIG. 10 is a side view of the radiator component.
Figure 11:
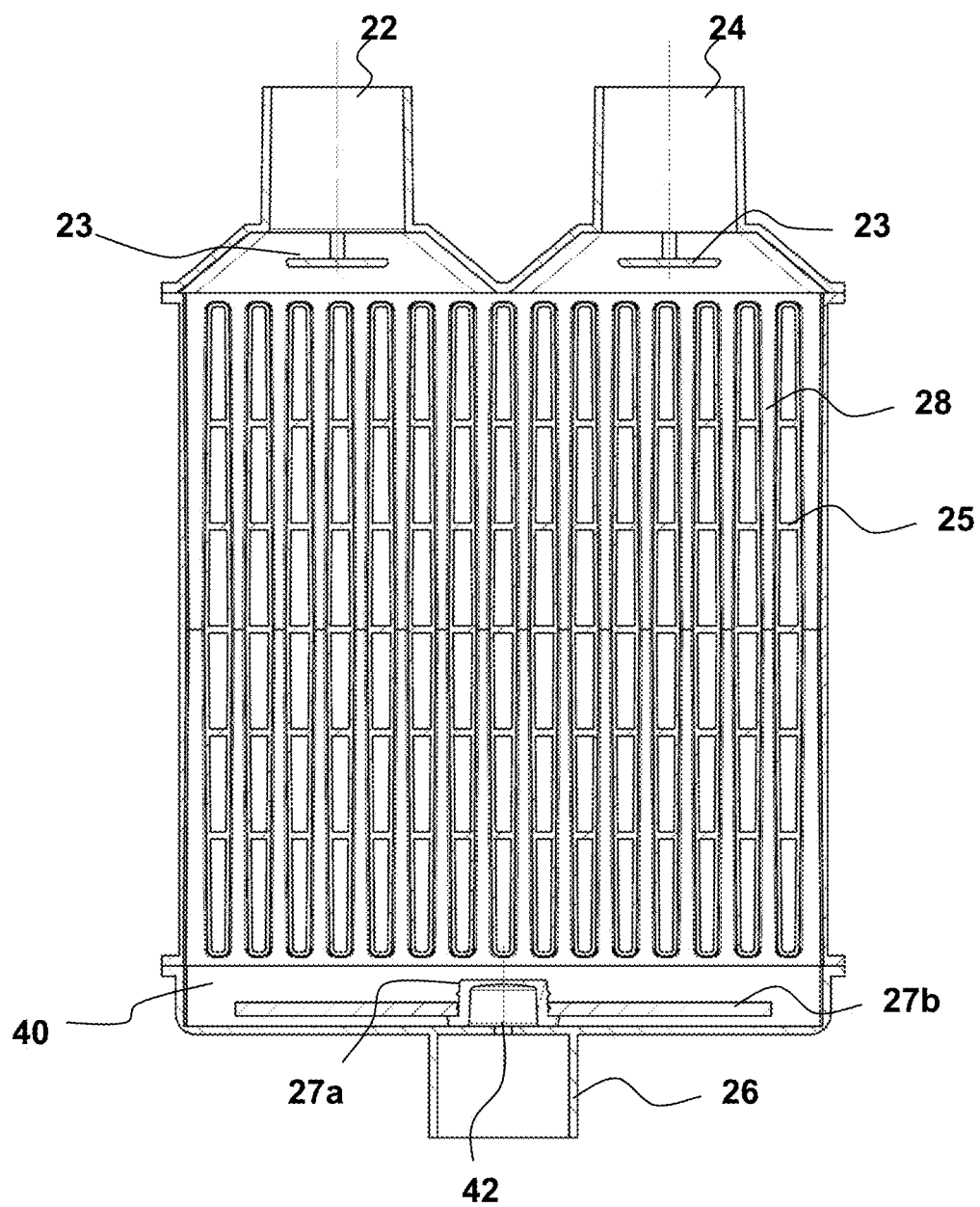
FIG. 11 is a cross sectional view of the radiator component along the line XI-XI in FIG. 10.

The radiator component 20 is shown engaged with the fan unit 30 in FIGS. 1 to 4, as well as in isolation in FIGS. 9 to 11. The radiator component 20 has an upper part that comprises an air inlet port 22 and an air outlet port 24 at its upper end, each having downwardly-extending, flared flow passages that are fixed to a peripheral flange at the upper end of an intermediate part of the radiator component 20. The air inlet port 22 and the air outlet port 24 are 22 mm tubular connectors, which are adapted to connect to conventional breathing tubes of an exhalation limb, in use. In addition, as shown in FIGS. 2 and 11, each of the flared flow passages extending downwardly from the ports 22,24 includes a circular baffle 23, which is generally planar in form, and disposed co-axially in relation to the associated port 22,24 and approximately mid-way down the flared flow passage. Each baffle 23 has a diameter that is slightly less than the diameter of the associated port 22,24, and acts to deflect incoming or outgoing respiratory gases transversely, such that the gas flow through the radiator component is more uniform across its width.

The intermediate part of the radiator component 20 has a peripheral flange at its upper end, which defines an opening that is in fluid communication with the air inlet port 22 and the air outlet port 24. At its lower end, the radiator component 20 has a peripheral flange that defines an opening in fluid communication with a lower part of the radiator component 20, which is discussed in more detail below.

Between the upper and lower flanges, the intermediate part of the radiator component 20 has a plurality of adjacent, but separate, flow passageways 28, which provide fluid communication between the upper and lower parts of the radiator component 20. Each flow passageway 28 is defined by an enclosing wall, which has an exterior surface that is in contact with ambient air.

Each flow passageway 28 extends vertically, and has a horizontal cross-sectional shape that is significantly elongated. In particular, the width of each flow passageway 28 (see FIG. 1) is of the order of 10 times less than the depth of each flow passageway 28 (see FIG. 3), such that each flow passageway 28 has the form of a generally planer, radiator fin that conveys respiratory gases, in use.

The flow passageways 28 of the radiator component 20 are orientated generally parallel to each other, with a regular separation between the enclosing walls of the flow passageways 28 that is approximately equal to the width of each flow passageway. The enclosing walls of adjacent flow passageways 28 are also joined by horizontal supporting webs 25, which are arranged in five rows, regularly spaced over the height of the flow passageways 28.

The arrangement of the flow passageways 28 and the supporting webs 25 is intended to maximize the exterior surface area of the enclosing walls that is in contact with the surrounding air. In addition, the flow passageways 28 and the supporting webs 25 are all orientated parallel to the direction of flow of air from the fan unit 30, as discussed in more detail below, such that air from the fan unit 30 flows through exterior passageways defined between the enclosing walls and the supporting webs 25.

The form of the flow passageways 28 is intended to optimize the internal surface area of the enclosing walls, to which heat from the respiratory gases is conducted. In addition, the arrangement of flow passageways 28 relative to the fan unit 30 is intended to optimize the external surface area of the enclosing walls that is subject to the air flow from the fan unit 30. This air flow from the fan unit 30 increases the rate of conduction of heat away from the enclosing walls by causing air to which heat from the enclosing walls has been conducted, and hence air that is at a raised temperature relative to ambient air, to be continuously replaced with ambient air at a lower temperature.

As shown clearly in FIG. 2, the radiator component 20 is adapted to be accommodated within a front portion 52 of the fan unit 30. In particular, the radiator component 20 comprises laterally opposed rails 29, which extend along a central, longitudinal axis of each side wall of the radiator component 20. The rails 29 are adapted to be slidably engaged with corresponding vertical grooves 32 in the front portion 52 of the fan unit 30, as discussed in more detail below.

The lower part of the radiator component 20 comprises a generally planer base, with an upstanding, peripheral skirt having an outwardly projecting flange at its upper end that is fixed to the flange at the lower end of the intermediate part of the radiator component 20. The lower part of the radiator component 20 therefore defines a chamber 40 disposed at the lower end of the flow passageways 28 of the radiator component 20, which acts as a sump for collecting water that condenses from the respiratory gases flowing through the radiator component 20, and flows down the flow passageways 28 under the influence of gravity.

The lower part of the radiator component 20 also includes a condensate outlet port 26, which extends from the external surface of the lower wall of the radiator component 20. The base of the radiator component 20 includes a central aperture 42, which enables condensate to exit the radiator component 20 via the condensate outlet port 26. The condensate outlet port 26 is therefore adapted to connect to suitable collection apparatus. In this embodiment, the condensate outlet port 26 has the form of a tubular connector.

In addition, the lower part of the radiator component 20 includes a simple float valve arrangement, which comprises a top-hat shaped sealing member 27a, which sits over the central aperture 42 in the base of the radiator component 20, and a generally rectangular, planar float member 27b extending outwardly therefrom.

The float-valve arrangement is adapted to allow condensate to flow through the central aperture 42, into the condensate outlet port 26, when the level of condensate within the lower part of the radiator component 20 is above a threshold level. In particular, when the level of condensate within the lower part of the radiator component 20 is above a particular level, the float member 27b and the sealing member 27a will be raised from the base of the radiator component 20 to a sufficient extent that condensate is able to flow through the central aperture 32, into the condensate outlet port 26. When the level of condensate within the lower part of the radiator component 20 falls back below the threshold level, the sealing member will be re-engaged with the base of the radiator component 20, and flow of condensate through the central aperture 42, into the condensate outlet port 26, will be prevented once again.

The fan unit 30 is shown with the radiator component 20 installed in FIGS. 1 to 4, as well as in isolation in FIGS. 5 to 8. The fan unit 30 comprises a housing having a rear portion 50 for accommodating a fan, and a front portion 52 for receiving the radiator component 20. The housing is formed in plastics material, and includes a cylindrical sleeve 36 within which a fan is mounted. The fan is not shown in the Figures, but would consist of a generally conventional electric fan, with a suitable electrical connection. In addition, the housing includes an integrally formed clip 54 on its rear surface, which is adapted to mount the fan unit 30 to a suitable rail, such as the rail of a ventilator machine.

The rear portion 50 of the fan unit 30 has a wall that surrounds the fan, but includes air inlet and air outlet arrangements 38,39 in its front and rear walls, respectively.

The air inlet arrangement 38 in the front wall of the rear portion 50 of the fan unit 30 comprises a generally rectangular opening, with a plurality of cross-members extending across the opening. The cross-members extend horizontally across the opening, and define generally horizontal outlet apertures that have a maximum height in a central, vertical region of the opening, and a gradually decreasing height towards each side. This arrangement results in a greater flow of air through a central, vertical region of the front wall of the rear portion 50 of the fan unit 30, and is adapted to provide a generally uniform flow of air through the radiator component 20.

The air outlet arrangement 39 in the rear wall of the rear portion 50 of the fan unit 30 comprises a generally circular opening, with a plurality of cross-members extending across the opening. The cross-members extend horizontally across the opening, and are generally planar members that are orientated at an angle to the rear wall, but generally parallel to each other, such that air blown through the opening is deflected downwardly relative to the fan unit 30.

The fan is adapted to draw air into the rear portion 50 of the fan unit 30 through the air inlet arrangement 38 described above, and expel that air through the air outlet arrangement 39 described above. In particular, the fan is arranged to draw air generally horizontally through the radiator component 20 and the air inlet arrangement 38, and expel that air from the fan unit 30 through the air outlet arrangement 39.

The front portion 52 of the fan unit 30 comprises a pair of opposing arms 56 that, together with the front wall of the rear portion 50 of the fan unit 30, define an enclosure for accommodating the radiator component 20.

As discussed above, the radiator component 20 comprises laterally opposed rails 29, which extend along a central, longitudinal axis of each side wall of the radiator component 20. The rails 29 are adapted to be slidably engaged with corresponding vertical grooves 32 in the front portion 52 of the fan unit 30. These vertical grooves 32 are formed approximately mid-way along the interior surface of each arm of the fan unit 30. This arrangement enables the radiator component 20 to be slidably engaged with the front portion 52 of the fan unit 30, from above.

The fan unit 30 also includes a ledge 34 at the lower end of front portion 52 of the fan unit 30. This ledge 34 projects from the lower end of the pair of opposing arms 56 of the fan unit 30, as well as the front wall of the rear portion 50 of the fan unit 30, and is continuous in form. The lower part of the radiator component 20 has a peripheral flange that projects outwardly from the lower part of the radiator component 20, as described above, which rests upon the ledge 34 when the radiator component 20 is fully engaged with the fan unit 30. The vertical grooves 32 and the ledge 34 of the front portion 52 of the fan unit 30 therefore cooperate with the rails 29 and the lower flange of the radiator component 20 to retain the radiator component 20 within the front portion 52 of the fan unit 30, but enable removal, and replacement, of the radiator component 20 by slidable disengagement and engagement of the radiator component with the fan unit 30 from above.

Once installed in the fan unit 30, the radiator component 20 has a fixed orientation relative to the fan unit 30 during operation of the apparatus. In particular, the radiator component 20 is arranged such that the flow passageways 28 of the radiator component 20, and the exterior flow passageways 28 defined between the flow passageways 28 and the supporting webs of the radiator component 20, are aligned with the direction of air flow from the fan unit 30. The increased air flow from a central, vertical region of the air outlet arrangement 38 of the fan unit 30 counteracts the spread of air flow that occurs, in use, following exit from the air outlet arrangement 38, such that the air flow through the radiator component 20 is generally uniform across its width.

The fan unit 30 is a reusable component, which is mounted to a rail of the respiratory apparatus providing ventilation of the patient, and connected to an appropriate power supply. The radiator component 20 is a single-use, disposable component, which is formed of plastics material. In use, the radiator component 20 forms part of a breathing circuit, and the radiator component 20 is engaged with the fan unit 30. The respiratory gases flowing through the radiator component 20 are cooled, which causes condensate to form and collect within the radiator component 20, and this condensate is removed from the breathing circuit through the condensate outlet port 26 using suitable collection apparatus. This use of the apparatus according to the invention is described in more detail below.

Figure 12:
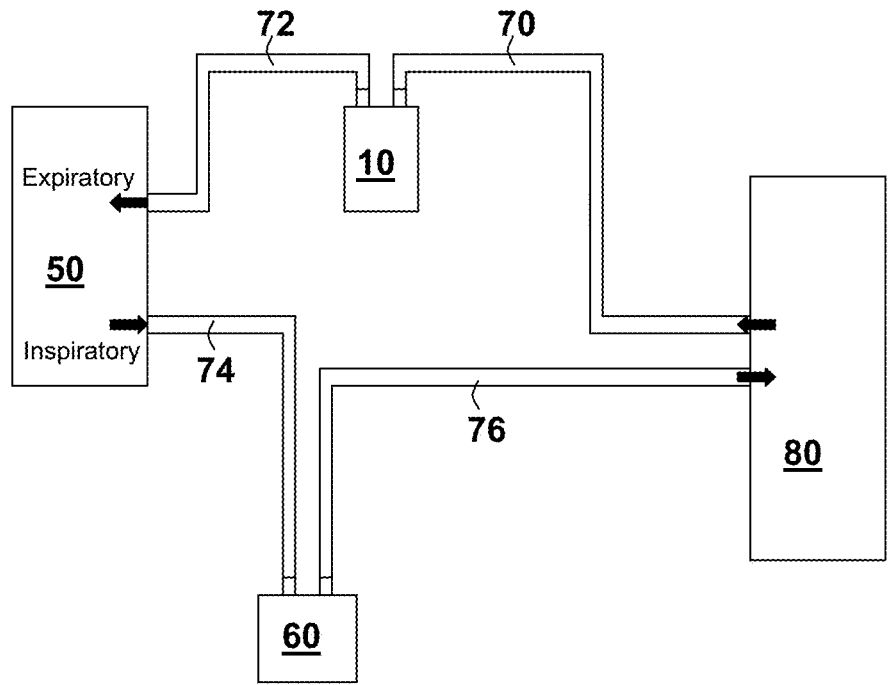
FIG. 12 is a schematic diagram of a respiratory circuit including the first embodiment.

FIG. 12 is a schematic diagram of an example breathing circuit including the apparatus 10 according to the invention. The breathing circuit comprises a ventilator 50, an inspiratory limb for delivering respiratory gases to a patient 80 for inhalation, and an expiratory limb for transporting exhaled respiratory gases back to the ventilator. The inspiratory limb comprises two breathing tubes 74,76, and a humidifier 60 between the two breathing tubes 74,76 for humidifying the respiratory gases before inhalation by the patient 80. The breathing tube 76 disposed between the humidifier 60 and the patient 80 is typically heated, in order to maintain the temperature and humidity of the respiratory gases at a desired level for inhalation.

The expiratory limb comprises two breathing tubes 70,72, and the dehumidifying apparatus 10 of the invention connected between the two breathing tubes 70,72 for removing water vapour from the exhaled respiratory gases before those respiratory gases are returned to the ventilator 50. Removal of water vapour from the exhaled respiratory gases in the expiratory limb of a breathing circuit reduces the risk of damage being caused to the ventilator by the water vapour, and also reduces the amount of condensation that occurs within the breathing tubes 70,72 of the expiratory limb, which may restrict or occlude the flow passageways of the breathing tubes 70,72.

In use, when the patient 80 exhales, expired air is carried along a first breathing tube 70 and enters the radiator component 20 of the dehumidifying apparatus 10 via the air inlet port 22. The expired air is deflected transversely by the baffle 23 in the flared passageway, and enters the flow passageways 28 that extend from the lower end of the flared passageway, on one side of the radiator component 20. The expired air flows down the flow passageways 28, to the chamber 40 in the lower part of the radiator component 20, and then flows up the flow passageways 28 on the other side of the radiator component 20, which lead to the air outlet port 24.

The provision of a plurality of flow passageways 28 within the radiator component 20, which each have a width that is significantly less than its length or depth, means that the internal surface area of the walls of the flow passageways 28, to which heat from the respiratory gases is conducted, is significantly increased relative to a conventional breathing tube, or a water trap chamber. The rate at which heat is conducted through the walls of the radiator component 20, to the ambient air, is therefore significantly increased.

In addition, the fan unit 30 causes air to flow through the exterior passageways defined between the enclosing walls of the flow passageways 28, and the supporting webs, of the radiator component 20. This air flow from the fan unit 30 increases the rate of conduction of heat away from the enclosing walls of the flow passageways 28 by causing air to which heat from the enclosing walls has been conducted, and hence air that is at a raised temperature relative to ambient air, to be continuously replaced with ambient air at a lower temperature.

The dehumidifying apparatus 10 therefore causes the respiratory gases flowing through the radiator component 20 to be cooled significantly, such that water vapour condenses into water within the radiator component 20, during use. The water condensate within the radiator component 20 flows down the flow passageways 28, into the chamber 40 in the lower part of the radiator component 20, where it collects. Once the level of condensate within the lower part of the radiator component 20 is above a threshold level, the float-valve arrangement of the radiator component 20 allows condensate to flow through the central aperture, into the condensate outlet port 26. The water condensate then flows into suitable collection apparatus.

Figure 13:
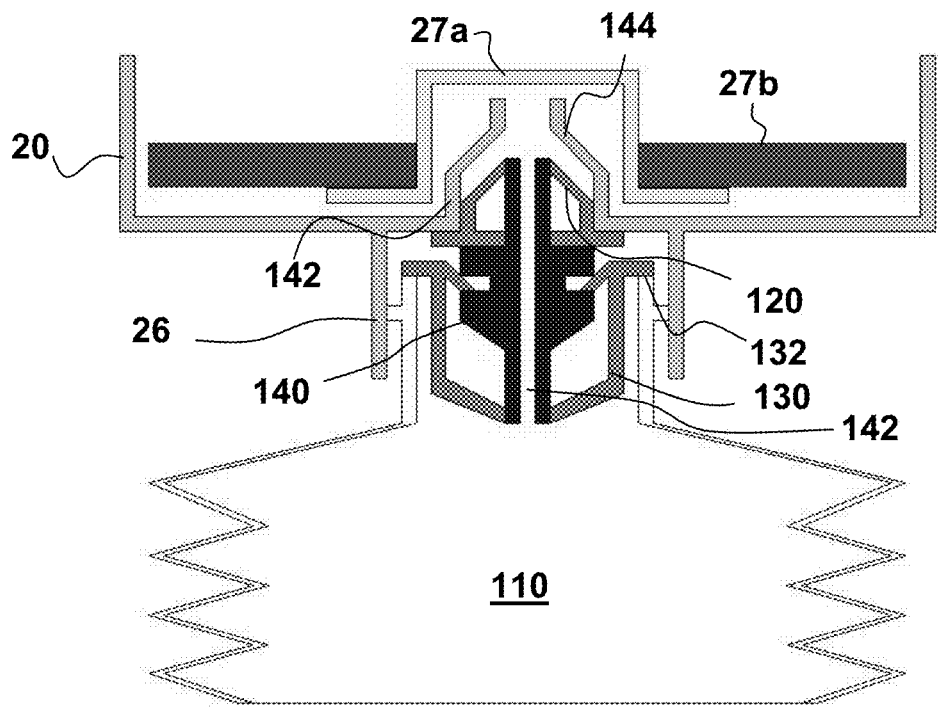
FIG. 13 is a schematic, cross sectional view of collection apparatus for use with the apparatus according to the invention.

One such collection arrangement is shown schematically in FIG. 13. In this arrangement, the base of the radiator component 20 includes an enlarged central aperture 142, and an upstanding spout 144 extends from the central aperture 142 that is closed by the sealing member 27a when the level of water is below the threshold level. Within the central aperture 142 and the condensate outlet port 26, the radiator component 20 is further provided with a valve arrangement that is opened by engagement of a collection vessel 110 with the condensate outlet port 26, and closed by removal of the collection vessel 110.

The valve arrangement comprises an upper duckbill valve 120, a lower duckbill valve 130, and a central connection member 140. The lower duckbill valve 130 includes an outwardly projecting flange 132 that is adapted to be engaged by the upper end of the collection vessel 110, on connection with the condensate outlet port 26, such that the outwardly projecting flange 132 of the lower duckbill valve 130 is urged upwardly. This action causes the lower duckbill valve 130 to be opened. In addition, this action causes the central connection member 140 to be moved upwardly, causing the upper duckbill valve 120 to open. The open configurations of the upper and lower duckbill valves 120, 130 define an outlet passageway 142 from the interior of the upstanding spout 144, into the condensate outlet port 26 and the collection vessel 110.

In this embodiment, the collection vessel 110 is adapted to connect to the condensate outlet port 26 by means of a bayonet connection. In addition, the collection vessel 110 has a bellows structure, such that the collection vessel 110 may be substantially evacuated before use, and expand during use as water condensate collects in the vessel 110.

Figure 14:
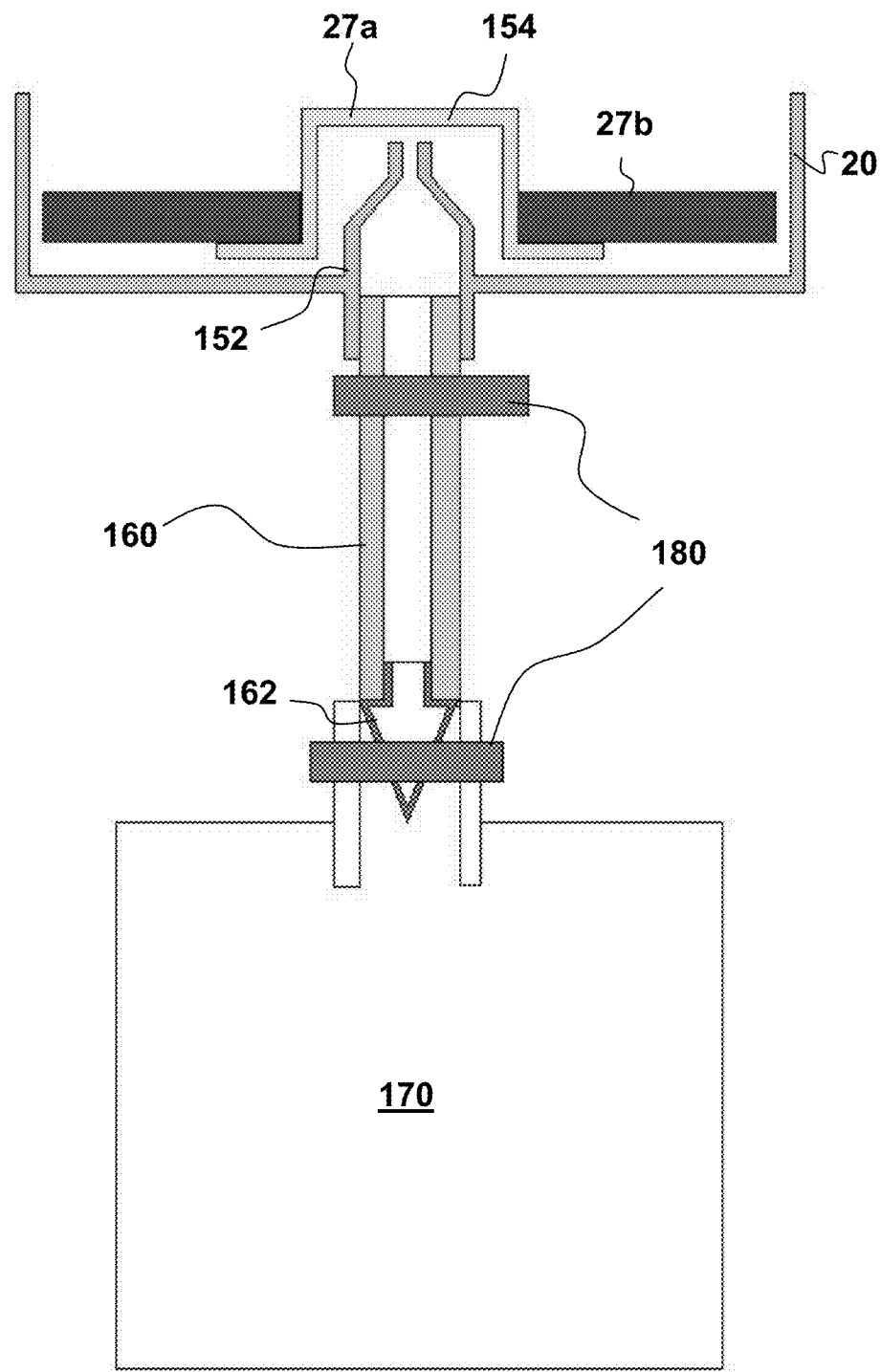
FIG. 14 is a schematic, cross sectional view of alternative collection apparatus for use with the apparatus according to the invention.

An alternative collection arrangement is shown schematically in FIG. 14. In this arrangement, the base of the radiator component 20 again includes an enlarged central aperture 152, and an upstanding spout 154 extending from the central aperture 152 that is closed by the sealing member 27a when the level of water is below the threshold level. In this arrangement, however, the condensate outlet port 26 has a reduced diameter, and is adapted to be connected to one end of a length of small bore tubing 160 that is conventionally using to deliver fluids in medical apparatus. The small bore tubing 160 is connected at its other end to a collection bag 170, within which water condensate is collected. A tube clamp 180 is provided at each end of the small bore tubing 160, which enables the tubing 160 to be closed when replacing the collection bag 170. Otherwise, the small bore tubing 160 remains open during use. A duckbill valve 162 is also provided within the end of the small bore tubing 160 that is connected to the collection bag 170.

A further development of this invention consists of the inclusion of a thermoelectric element, and specifically a Peltier device, in the base unit of the apparatus, and the provision of both a condensation chamber and a downstream heater chamber in the heat exchange module. In this arrangement, the cold side of the thermoelectric element cools the respiratory gases in the condensation chamber, and the hot side of the thermoelectric element warms the respiratory gases in the downstream heater chamber. This heating of the respiratory gases before exiting the heat exchange module reduces the likelihood that any remaining vapour within the gas flow will condense out of the gas flow within another portion of the breathing system.

A second embodiment of apparatus according to the invention is described in detail below, with reference to FIGS. 15 to 20.

FIGS. 15 to 20 each show dehumidification apparatus according to the invention, which is generally designated 226. The apparatus comprises a base unit 232 and a removable/replaceable cartridge 234. The cartridge 234 may otherwise be considered to constitute a gas flow vessel or flow chamber.

The cartridge 234 generally comprises a thin-walled, hollow member shaped to define an internal gas-filled void. The cartridge 234 provides a gas-tight chamber with the exception of the ports 228, 230 and 236. The ports 228 and 230 provide respective inlet and outlet ports for the flow of respiratory gas into and from the cartridge 234 in use. The port 236 is a liquid drainage port, the details of which will be described below.

Figure 3:
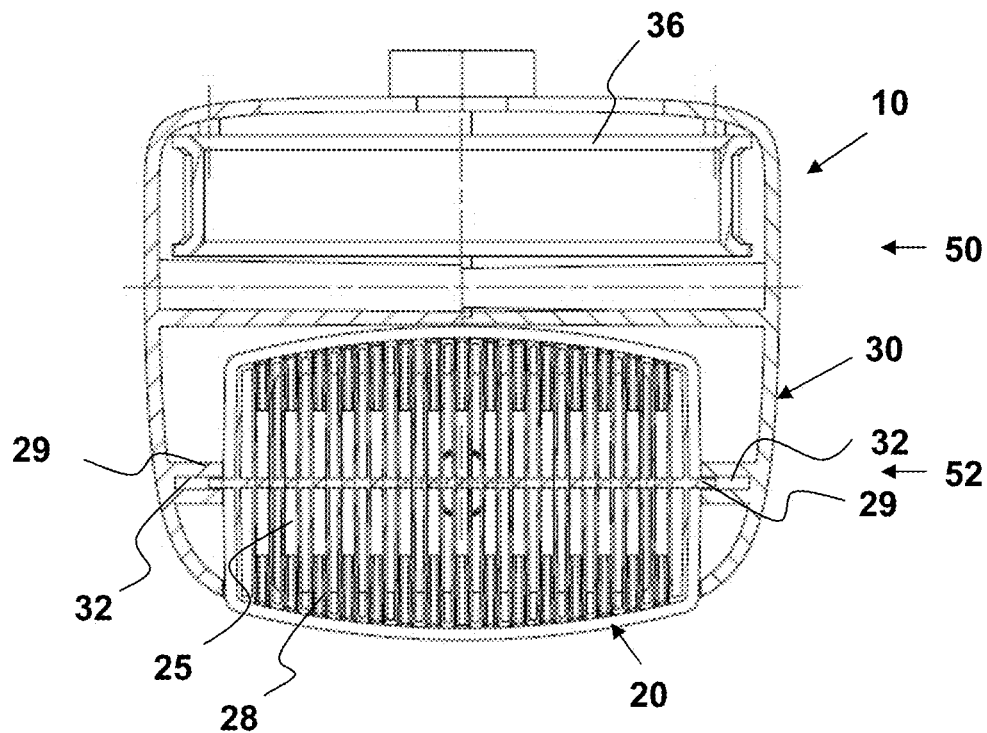
FIG. 3 is a cross sectional view of the first embodiment along line III-III in FIG. 1.
Figure 4:
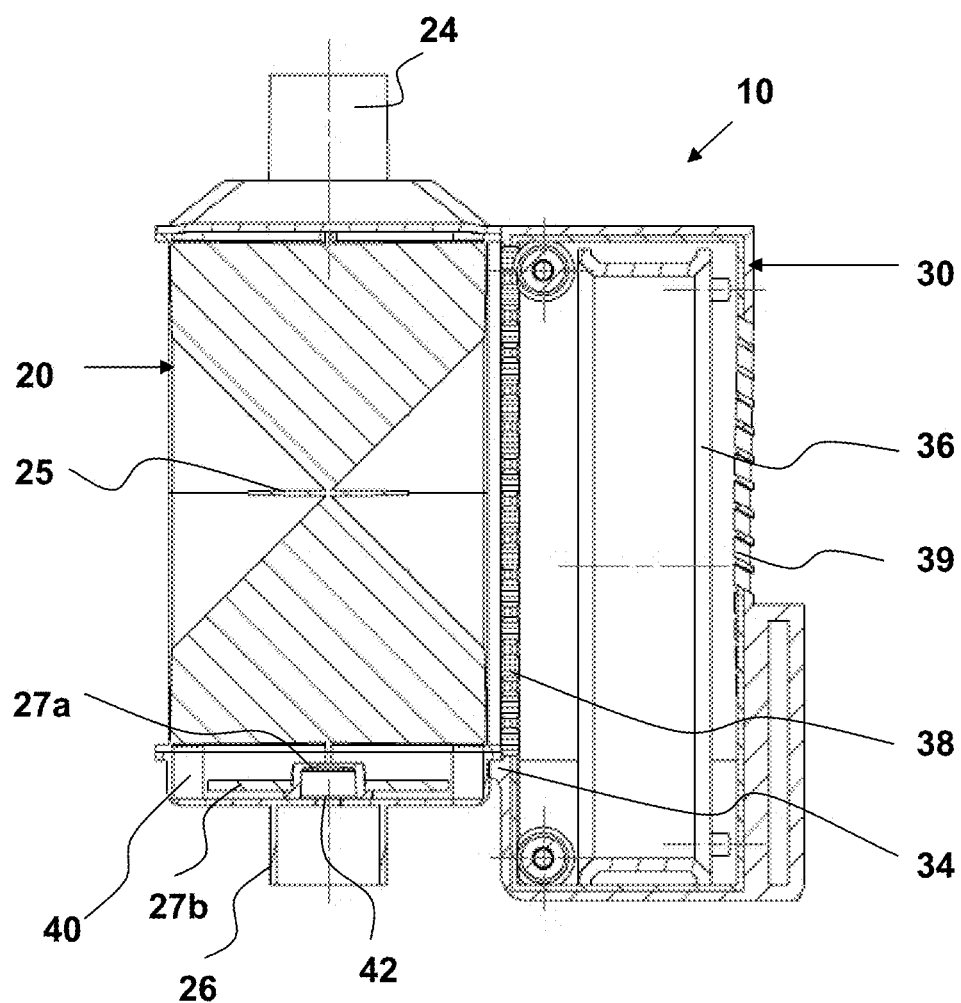
FIG. 4 is a cross sectional view of the first embodiment along the line IV-IV in FIG. 1.
Figure 5:
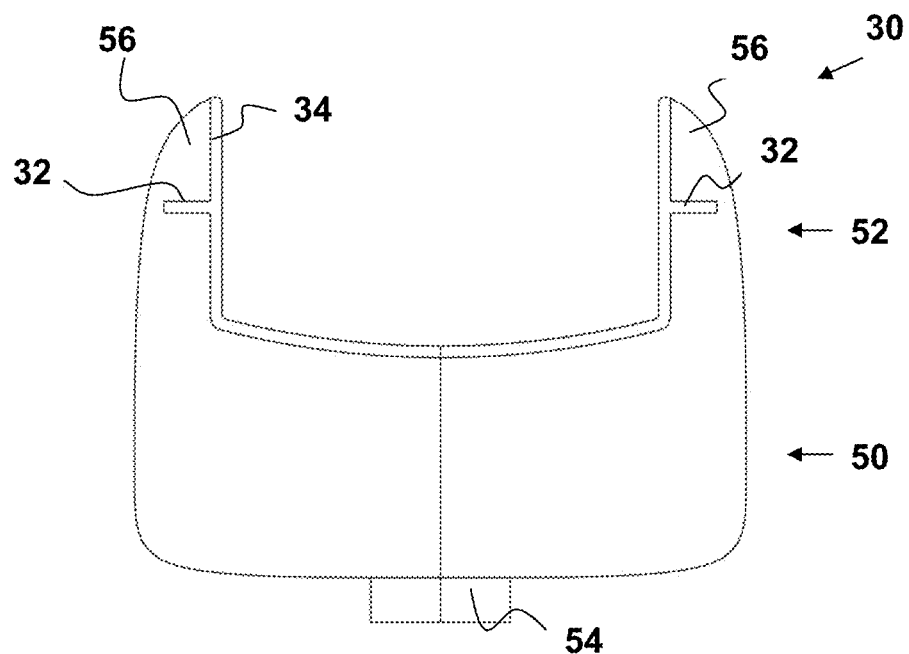
FIG. 5 is a plan view of a fan unit, which forms part of the first embodiment.
Figure 6:
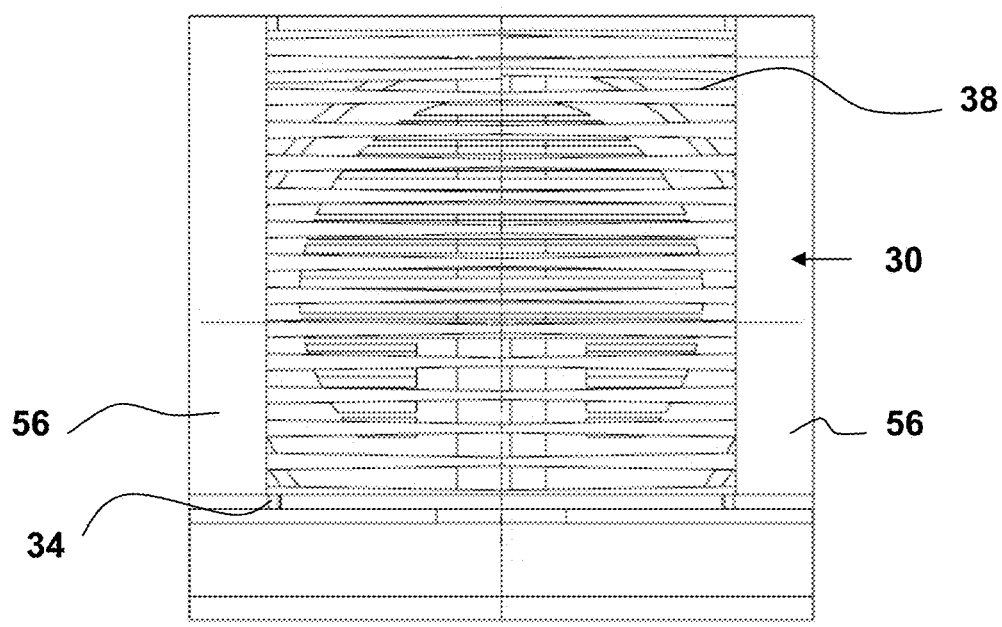
FIG. 6 is a front view of the fan unit.
Figure 7:
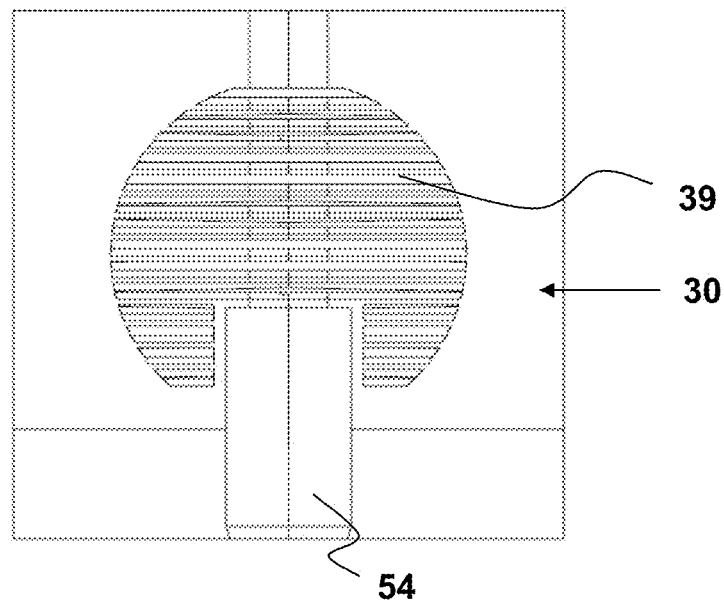
FIG. 7 is a rear view of the fan unit.
Figure 8:
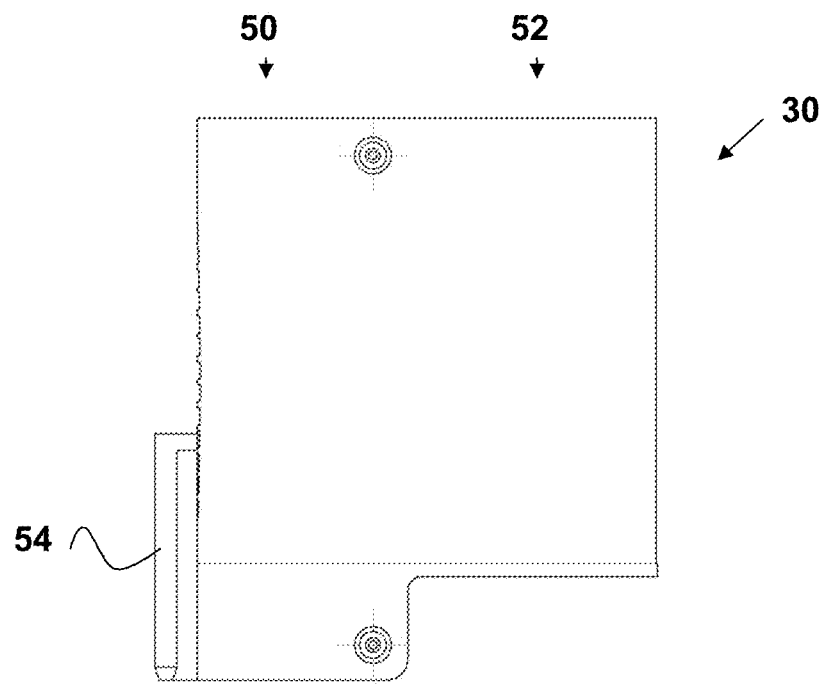
FIG. 8 is a side view of the fan unit.
Figure 15:
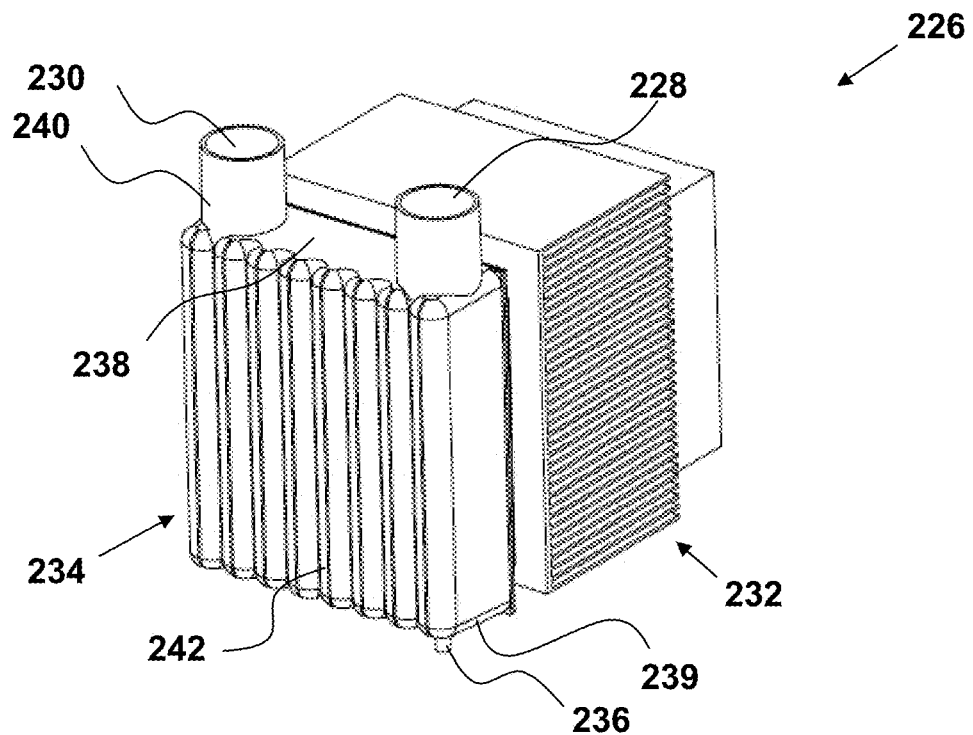
FIG. 15 is a three-dimensional view from the front of a second embodiment of apparatus according to the invention.

The ports 228 and 230 are provided in a common outer wall 238 of the cartridge 234, which wall in use is typically arranged to provide an upper, or upwardly facing, wall of the cartridge 234. An opposing, lower wall 239 is provided, which constitutes the base of the cartridge 234 in an in-use orientation as shown in FIGS. 2 and 3. The ports 228 and 230 are provided with respective upstanding connector formations 240, which each take the form of an annular wall depending from the wall 238. The connectors 240 are of conventional size to closely and securely fit with the ends of breathing tubes 222 and 224 as shown in FIG. 15. When connected in this manner, the internal chamber of the cartridge 234 is sealed from ambient air and/or any external devices such that the interior of the cartridge 234 forms a part of the closed flow path of the respiratory system shown in FIG. 15.

The cartridge 234 is preferably formed of a suitably rigid plastic material, for example by injection moulding.

The cartridge 234 is generally rectangular in plan and has a substantially continuous front wall 242, which faces away from the base unit 232 when the cartridge is mounted thereon for use.

The opposing (rear) wall 244 of the cartridge, which faces the base unit 232 has a series of longitudinal slots or recesses therein. In this regard the wall structure of the cartridge 234 is shaped to provide a plurality of wall projections 248 which protrude from the rear wall 244 into the internal volume of the cartridge 234. Those projections 248 thus reduce or 'eat into' the internal volume of the cartridge 234. The wall projections 248 can be seen from above in FIG. 19 through the ports 228, 230.

The flow channels thus present a large internal wall surface area to the flow passing through the cartridge so as to increase the area available for heat transfer to/from the flow in use.

Figure 16:
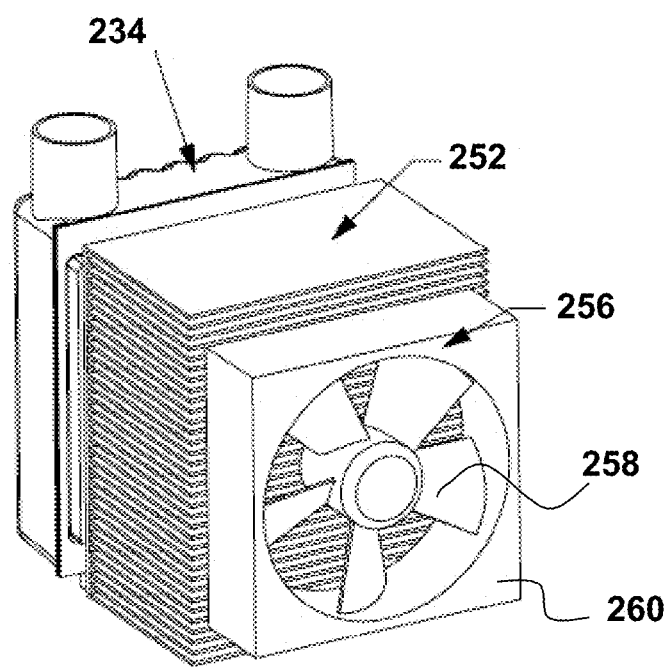
FIG. 16 is a three-dimensional view from the rear of the second embodiment.

Turning now to FIGS. 16 and 18, there are shown further details of the base unit 232 which comprises a heat-dissipating structure comprising a series of generally planar fins 252 depending from a support plate 254. The fins 252 are generally upstanding from the support plate, typically perpendicularly thereto. The fins 252 are spaced along the plate 254 and generally parallel in alignment such that each fin 252 is spaced from an adjacent fin 252 by an air-gap.

Each fin 252 is supported only along one edge by the plate 254 such that the further sides of the heat-dissipating structure, comprising of the aligned edges of the fins, are open. The fins and support plate are formed of metal as a unitary structure and may be unitarily formed.

A fan unit 256 is mounted on the rear side of the heat dissipating structure. The rear side is the open side of the structure which opposes, or faces away from, the support plate 254. The fan unit 256 comprises a fan 258 arranged for rotation within a fan housing 260, by which the fan unit 256 is attached to the heat dissipating structure. The fan unit 256 is electrically powered to drive the fan in rotation in a direction which draws ambient air through the fins and expels air to the surroundings, typically in a direction away from the apparatus 226. In the orientation shown in FIG. 16, the fan 256 rotates anti-clockwise.

Turning now to FIGS. 17 and 20, there are shown respective views of the base unit 232 with and without the cartridge 234 attached. A heat transfer structure 262 is provided between the heat dissipating structure and the cartridge 234. The heat transfer structure depends from the support plate 254 in a direction facing away from the fan unit 256.

The heat transfer structure 262 comprises a heat transfer element or heat pump 264, which is arranged between thermal conductors 266 and 268. In this embodiment, the heat pump 264 is a thermoelectric heating/cooling device, which takes the form of a Peltier device. Such a device may otherwise be described as a solid-state active heat pump. The Peltier device has opposing major faces which are plate-like conductors and a plurality of thermoelectric elements therebetween (not shown), which are arranged electrically in series but thermally in parallel between the opposing plate conductors. Accordingly the supply of electric power to the device drives a temperature difference between the conductor plates such that a first plate conductor comprises a cold side of the device and the opposing conductor comprises a hot side of the device.

The cold side of the Peltier device 264 is connected to the conductor arrangement 266. This conductor arrangement comprises a plurality of projections 270 depending away from the Peltier device. The projections 270 are spaced in a series or configuration which corresponds to the recesses 246 in the rear wall of the cartridge. The projections 270 are elongate in form and upstanding akin to fins or finger-like formations which are shaped to form a close fit with the wall projections of the cartridge 234 and thereby form a good thermal contact therewith. The projections 270 depend from a generally planar backing portion which forms a thermal contact over the area of the cold side of the Peltier device for heat transfer therewith.

The hot side of the Peltier device 264 is connected to conductor formation 268, which comprises a relatively thin walled or planar body 272 which is sandwiched between the hot side of the Peltier device 264 and the back/support plate 254 of the heat dissipating structure. Towards an edge of the body 272 (i.e. towards the right hand edge as shown in FIG. 20), there are provided further upstanding projections 274. The projections 274 project outwardly from the body 272 in the same direction as the projections 270. The projections 274 in this embodiment are shaped and spaced in a manner which corresponds to that of the projections 274. Hence the projection 270 and 274 are substantially the same shape.

However, it can be seen that there are fewer of the projections 274 than there are of projections 270. In this embodiment, the ratio between the projections 270 and 274 is 3:1, such that there are six 'cold' projections 270 and only two 'hot' projections 274. However different ratios and/or numbers of projections 270,274 may be provided as necessary. The combined array of the projections 270 and 274 is arranged for insertion into the recesses 246 in the cartridge, such that some of the recesses are filled by the projections 270 and other recesses are filled by projections 274. It is notable that the projections 270 are grouped, as are the projections 274 such that those different types of projections are not interspersed.

The cartridge 234 is mounted for use to the base unit 232 by aligning the projections 270, 274 with the recesses in the rear wall of the cartridge 234 and then moving the cartridge 234 rearwardly (in the direction of arrow A in FIGS. 17 and 18) such that the projections slot into the recesses. In alternative embodiments, the cartridge 234 could be slid over the projections 270,274 in the longitudinal direction. In either embodiment, the cartridge 234 and/or projections 270,274 could be provided with one alignment grooves or ridges to ensure a close/tight fitment between the cartridge 234 and base unit 232.

In readiness for use, the ports 228 and 230 are connected to the respective tubes 70 and 72 in the respiratory system as shown in FIG. 12. The base unit 232 is also connected to a power supply, which typically comprises a connection to a mains power supply by a suitable lead (not shown), such that electrical power is supplied to the Peltier device 264 and fan unit 256. The supply of power to the Peltier device 264 drives a temperature difference between the opposing sides of the device by thermoelectric effect, thereby cooling the projections 270, whilst heating projections 274.

Thus, in use, when a cartridge 234 is located on the device such that it is in thermal conductive contact with the projections 270,274, a first plurality of the internal wall portions 248 are cooled by projections 270, whist a second plurality of wall portions of the cartridge are heated by projections 274. This results in the internal cavity of the cartridge in use having a cooled region upstream of a heated region. Thus the gas entering the cartridge 234 at the inlet port 228 is first cooled by the walls of the cartridge 234, promoting condensation of the vapor within the expired gas flow from the patient. In this regard, the gas flow is typically cooled to at or below its due point, such that condensation readily occurs on the internal walls of the cartridge.

Although the cartridge is formed of a generally thin-walled structure, it is noted that the rear wall 244 and/or wall projections 248 which define the recesses in the cartridge are particularly thin walled and may have a wall thickness that is lower than that of the remainder of the cartridge. This is to ensure a low impedance to heat transfer from the gas flow to/from the base unit projections 270, 274.

Once the gas flow passes the final cooled internal wall projection in the cartridge, the gas then enters heated flow passages defined by the downstream internal cartridge walls that are heated by the base unit heater projections 274. Thus heat energy removed from the gas flow by the Peltier device 264 is conducted back to the downstream walls of the cartridge via conductor 272 and projections 274 so as to reheat the gas flow to above its dew point before the gas exits the cartridge via the outlet port.

The multiple flow channels caused by the internal baffles within the cartridge 234 provides a large surface area for extracting heat energy from the gas flow. Also the channels within the cartridge 234 define a flow path for the gas such that the heated portion of the cartridge chamber is arranged downstream in flow series from the cooled cartridge portion. This helps to ensure that heat is not transferred to the cooled section by either conduction or else convection.

It has been found that the amount of heat generated by the Peltier device is greater than the amount of heat energy needed to reheat the gas flow to above its dew point. Accordingly the connection between the body 272 on the hot side of the Peltier device and the heat dissipating structure 232 allows excess heat to be lost to the ambient air. Thus the heat dissipating structure acts as a heat sink for the system. The rate of heat loss to ambient air is increased by the airflow caused by fan 58.

It is a notable advantage that the interior of the cartridge 234 is closed from the base unit 232 such that the above described heat transfer functions are achieved within the cartridge 234, whilst avoiding exposure of the remainder of the base unit 232 to the respiratory gas flow. This allows the cartridge 234 to be provided as a replaceable, and typically disposable, component, which can be removed from the base unit 232 after use. The base unit 232 can thus be reused by attaching a new cartridge thereto in the manner described above.

The condensate within the condensing portion of the cartridge interior gathers on the internal walls and runs down to the base wall 239 of the cartridge under the action of gravity. Accordingly, a condensate collection arrangement is provided which communicates with the cartridge via the port connector 236 shown in FIG. 17. This condensate collection arrangement may have either of the forms described above, with reference to FIGS. 13 and 14.

The second embodiment of the apparatus, which is described above, would be constructed with the base unit 232 being housed within a casing (not shown in the Figures). The casing would include an arrangement for releasably engaging the cartridge 234. In particular, the projections 270,274 of the conductor arrangement would be exposed, such that the cartridge 234 may be replaceably engaged with those projections 270,274. The casing would also include flow outlets for the air emitted by the fan 258 to exit the apparatus.

Figure 21:
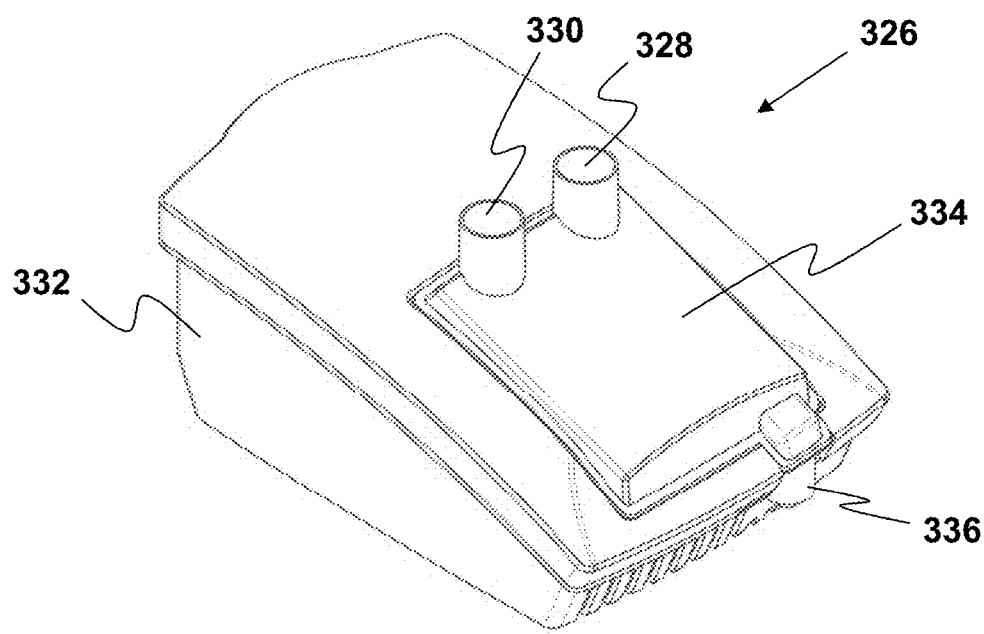
FIG. 21 is a three-dimensional view from the front of a third embodiment of apparatus according to the invention.

FIG. 21 shows a third embodiment of dehumidification apparatus according to the invention, which is generally designated 326. The apparatus 326 is similar to the second embodiment described above. However, in this embodiment, the base unit 332 is shown with a casing, which houses an arrangement that is almost identical to the base unit 232 described above in relation to the second embodiment 226, and hence including a heat exchange device (Peltier device), an associated conductor arrangement, a fan unit and an associated heat sink.

The principal difference between the base unit 332 of the third embodiment and that of the second embodiment is that the base unit 332 is provided with a number of projections 374 that are in communication with the hot side of the heat exchange device (Peltier device) that is equal to the number of projections 370 that are in communication with the cold side of the heat exchange device (Peltier device). These projections 370,374 are visible in FIG. 22.

Figure 22:
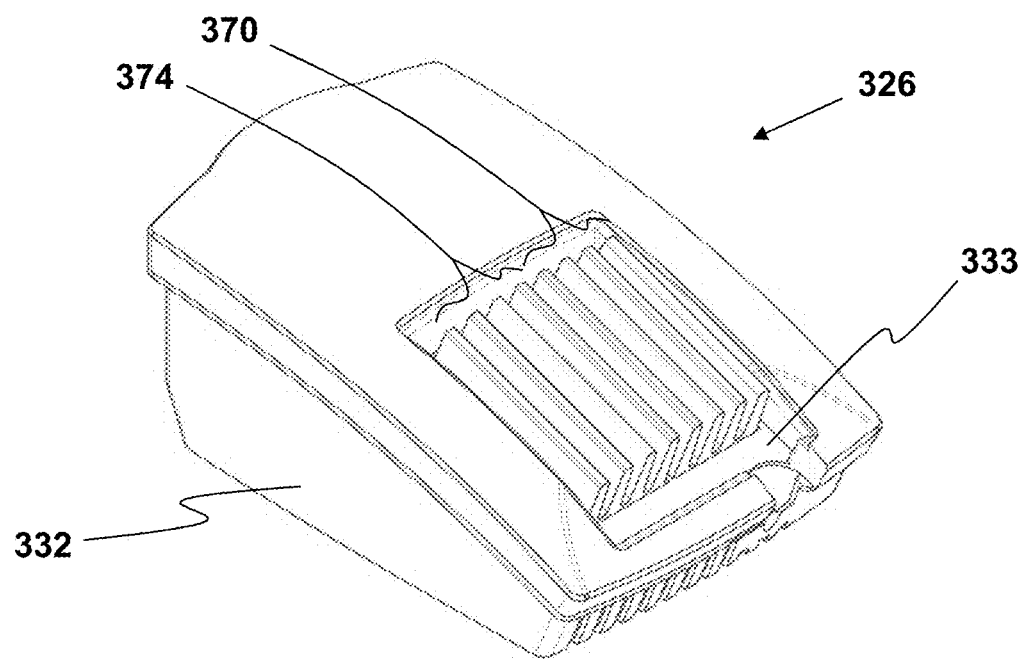
FIG. 22 is a three-dimensional view from the front of the base unit of the apparatus of FIG. 21.

As shown in FIG. 22, the base unit 332 includes a generally rectangular recess 333, of substantially uniform depth, in its upper wall for receiving the cartridge 334. The two sets of projections 370,374 that are in communication with the heat exchange device (Peltier device) 370,374 project from respective openings in the floor of the recess 333, such that these projections 370,374 are upstanding within the recess 333. The recess 333 is arranged at an oblique angle relative to the surface on which the base unit 332 rests, such that the cartridge 334 is arranged at an oblique angle relative to horizontal, in use, and water drains down to the liquid drainage port 336.

The base unit 332 also includes a series of parallel, rectangular openings on its front wall, which serve as outlets for the airflow generated by the fan of the base unit 332.

Figure 23:
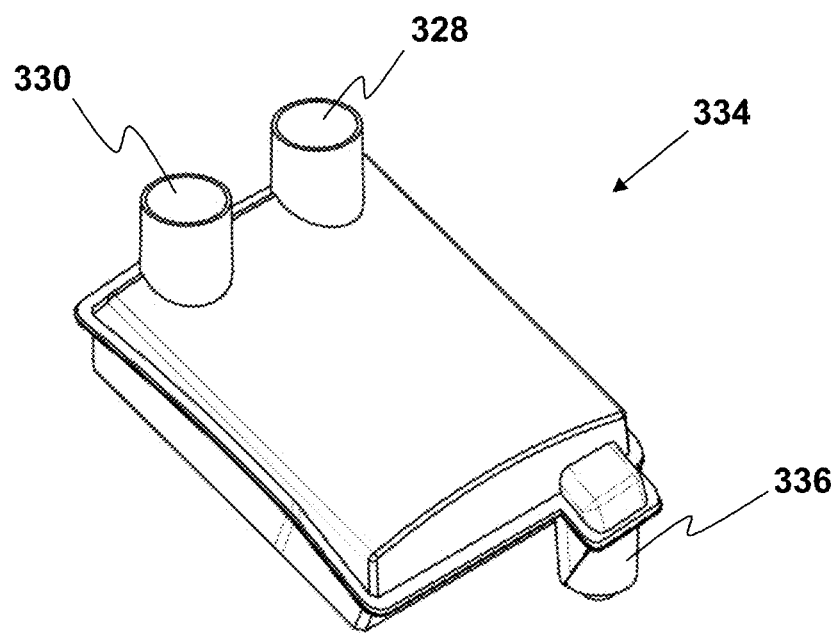
FIG. 23 is a three-dimensional view from above the cartridge of the apparatus of FIG. 21.
Figure 24:
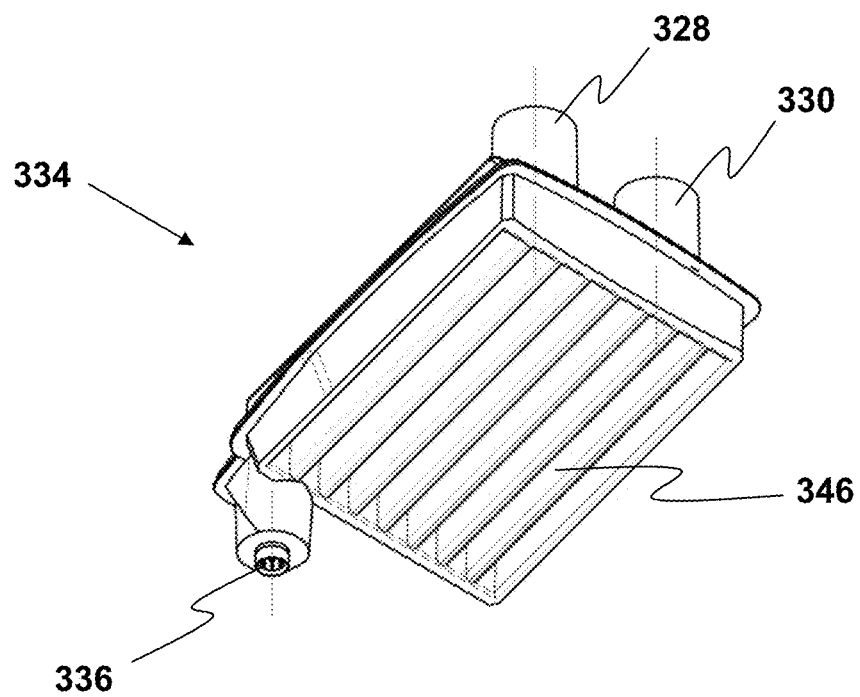
FIG. 24 is a three-dimensional view from below the cartridge of the apparatus of FIG. 21.

As shown in FIGS. 23 and 24, the cartridge 334 is formed of two injection moulded components, which define a flow chamber extending between an inlet port 328 and an outlet port 330. The inlet and outlet port 328 and 330 extend parallel to each other, from one end of an upper surface of the cartridge 334, such that these ports project upwardly from the apparatus 326 when the cartridge 334 is engaged with the base unit 332. At the other end of the cartridge 334, a liquid drainage port 336 extends in the opposite direction to the inlet and outlet ports 328,330, such that the liquid drainage port 336 extends downwardly at one end of the base unit 332, when the when the cartridge 334 is engaged with the base unit 332.

The lower wall of the cartridge, which is visible in FIG. 24, is formed with a plurality of parallel recesses 346, which in turn causes the flow chamber to include a plurality of respective projections. These recesses 346 correspond in number, namely eight, and to the number of projections 370,374 in the recess 333 in the upper wall of the base unit 332, and have a corresponding form, such that these recesses 346 receive the projections 370,374, with a close fit, when the cartridge is engaged with the recess 333. In particular, the exterior surface of the lower wall of the cartridge 334 having these recesses 346 is in contact with the external surface of the projections 370,374 of the base unit 332 to enable effective heat transfer between the cartridge 334 and the base unit 332.

As discussed above, the two sets of projections 370,374 that are in communication with the heat exchange device (Peltier device) 370,374 project from respective openings in the floor of the recess 333, and contact the lower wall of the cartridge 334. Each set of projections 370,374 consists of four parallel projections 370,374, which engage with respective halves of the lower wall of the cartridge 334. In particular, the projections 370 that are in communication with the cold side of the heat exchange device (Peltier device) are in contact with the half of the cartridge 334 into which the inlet port 328 extends, and the projections 374 that are in communication with the hot side of the heat exchange device (Peltier device) are in contact with the half of the cartridge 334 into which the outlet port 330 extends. In this arrangement, as in the arrangement of the first embodiment, the respiratory gases entering the cartridge through the inlet port 328 are firstly cooled by heat transfer to the 'cold' set of projections 370, through the lower wall of the cartridge 334, thereby causing water to condense and flow down to the liquid drainage port. The respiratory gases then pass into the other half of the cartridge 334, and are heated by heat transfer from the 'hot' set of projections 370, through the lower wall of the cartridge 334, such that water no longer condenses. The respiratory gases then exit the cartridge 334 through the outlet 330.

The invention claimed is:

1. Apparatus for condensing water from respiratory gases, comprising a heat exchange component having an inlet, an outlet and a condensation chamber, the inlet and outlet being connectable to a breathing system, such that respiratory gases are conveyed through the condensation chamber, in use, and a base unit adapted to aid removal of heat from the walls of the heat exchange component, wherein the heat exchange component is releasably engageable with the base unit, such that the heat exchange component is replaceable, wherein the heat exchange component forms a closed system relative to the base unit, such that there is no contact between the base unit and the respiratory gases, and wherein the heat exchange component includes a water condensate outlet port, which is adapted to enable removal of water condensate from the heat exchange component.

2. The apparatus of claim 1, wherein the water condensate outlet port allows a flow of water condensate out of the heat exchange component, without allowing a flow of respiratory gases through the water condensate outlet port.

3. The apparatus of claim 1, wherein the water condensate outlet port, or a fluid conduit connected thereto, includes a duckbill valve.

4. The apparatus of claim 1, wherein the apparatus includes a sump component that is removably connected to the water condensate outlet port of the heat exchange component.

5. The apparatus of claim 4, wherein the apparatus includes a valve for closing the water condensate outlet port when the sump component is removed for emptying or disposal.

6. The apparatus of claim 5, wherein the valve includes one or more duckbill valves, which are maintained in an open configuration by the presence of the sump component in connection with the heat exchange component, and which revert to a closed configuration when the sump component is disconnected from the heat exchange component.

7. The apparatus of claim 6, wherein the sump component is adapted to cause the movement of resiliently movable, outwardly extending arms of the valve on connection of the sump component to the heat exchange component.

8. The apparatus of claim 6, wherein the valve includes two duckbill valves, which are coupled by a connection member, such that connection of the sump component to the heat exchange component causes both duckbill valves to open.

9. The apparatus of claim 1, wherein the water condensate outlet port includes a float valve, which prevents a flow of water condensate out of the heat exchange component when the level of water condensate within the heat exchange component is below a threshold level and allows the flow of water condensate out of the heat exchange component when the level of water condensate within the heat exchange component is at or above the threshold level.

10. The apparatus of claim 1, wherein the heat exchange component is a disposable component.

11. The apparatus of claim 1, wherein the heat exchange component is formed of plastics material.

12. A heat exchange component for condensing water from respiratory gases and having an inlet, an outlet and a condensation chamber, the inlet and outlet being connectable to a breathing system, such that respiratory gases are conveyed through the condensation chamber, in use, wherein the heat exchange component is releasably engageable with a base unit adapted to aid removal of heat from the walls of the heat exchange component, wherein the heat exchange component forms, in use, a closed system relative to said base unit, such that there is no contact between the base unit and the respiratory gases, and wherein the heat exchange component includes a water condensate outlet port, which is adapted to enable removal of water condensate from the heat exchange component.

13. A breathing system comprising the apparatus of claim 1.

14. A breathing system comprising the heat exchange component of claim 12.

15. The breathing system of claim 14, wherein the breathing system is a breathing circuit comprising a ventilator or an anesthetic machine, an inspiratory limb, and an expiratory limb.

16. The breathing system of claim 15, wherein an apparatus for condensing water from respiratory gases, comprising the heat exchange component is connected within the breathing circuit, such that it forms part of the expiratory limb.

* * * * *